United States Patent [19]
Koerner et al.

[11] Patent Number: 6,033,856
[45] Date of Patent: Mar. 7, 2000

[54] PROMOTER OF THE CDC25B GENE, ITS PREPARATION AND USE

[75] Inventors: Kathrin Koerner; Rolf Mueller; Hans-Harald Sedlacek, all of Marburg, Germany

[73] Assignee: Hoechst Aktiengesellschaft, Frankfurt am Main, Germany

[21] Appl. No.: 09/039,555

[22] Filed: Mar. 16, 1998

[30] Foreign Application Priority Data

Mar. 14, 1997 [DE] Germany .......................... 197 10 643

[51] Int. Cl.$^7$ .............................. C07H 21/04; C12N 5/10; C12N 15/85
[52] U.S. Cl. ........................... 435/6; 435/320.1; 435/325; 435/357; 435/366; 536/23.1; 536/24.1
[58] Field of Search ........................... 435/6, 320.1, 325, 435/357, 366; 514/44, 2; 530/350; 536/23.1, 23.2, 23.4, 23.5, 24.1

[56] References Cited

FOREIGN PATENT DOCUMENTS

| | | |
|---|---|---|
| WO96/06940 | 3/1996 | WIPO . |
| WO96/06941 | 3/1996 | WIPO . |
| WO96/06943 | 3/1996 | WIPO . |
| WO96/069938 | 3/1996 | WIPO . |

OTHER PUBLICATIONS

Jelkmann (1994) Biology of erythropoietin. Clin. Investig. 72:S3–S10, 1994.

Verma et al. (1997) Gene therapy–promises, problems and prospects. Nature 389:239–242, Sep. 1997.

Aulitzky et al., Interleukins Clinical Pharmacology and Therapeutic Use, *Drugs* 48:667 (1994).

Augustin–Voss et al., Migrating Endothelial Cells Are Distinctly Hyperglycosylated and Express Specific Migration–associated Cell Surface Glycoproteins, *J. Cell Biol.*, 119:483 (1992).

Berling et al., Cloning of a Carcinoembryonic Antigen Gene Family Member Expressed in Leukocytes of Chronic Myeloid Leukemia Patients and Bone Marrow *Cancer Res.*, 50:6534 (1990).

Blackwood et al., Max: A Helix–Loop–Helix Zipper Protein That Forms a Sequence–Specific–DNA–Binding Complex with Myc, *Science* 251:1211, (1991).

Bogerd et al., Identifiation of a Novel Cellular Cofactor for the Rev/Rex Class of Retroviral Regulatory Proteins, *Cell* 82:485 (1995).

Brown et al., Redundancy of Signal and Anchor Funcitons in the NH$_2$–Terminal Uncharged Region of Influenza Virus Neuraminidase, a Class II Membrand Glycoprotein, *J. Virol.*, 62:3924 (1988).

Burrows et al., Vascular Targeting–A New Approach To The Therapy of Solid Tumors, (*Pharmac. Ther.*, 64:155 (1994).

Chasman et al., GAL4 Protein: Purification, Association with GAL80 Protein, and Conserved Domain Structure, *Mol. Cell. Bio.*, 10:2916 (1990).

Christoffersen et al., Ribozymes as Human Therapeutic Agents, *J. Med. Chem.*, 38:2033 (1995).

Cosman et al., Human Macrophagre Colony Stimulating Factor (M–CSF): Alternate RNA Splicing Generates Three Different Proteins That Are Expressed on the Cell surface and Secreted, *Behring Inst. Mitt.*, 77:15 (1988).

Cross et al., Growth Factors in Development, Transformation, and Tumorigenesis, *Cell*, 64:271 (1991).

Deonarain et al., Targeting enzymes for cancer therapy: old enzymes in new roles, (*British Journal Cancer*, 70:786 (1994).

Dingwall et al., Nucler Targeting Sequences a–consensus *TIBS* 16:78 (1991).

Donnelly et al., Immunization with Polynucleotides "A Novel Approaoch to Vaccination" *Immunol.* 2;20 (1994).

Drexler et al., The Use of Monoclonal Antibodies for the Identificagtion and Classification of Acute Myeloid Leukemias, *Leuk. Res.*, 10:279 (1986).

Drexler et al., Routine Immunophenotyping of Acute leukaemias, *Blut*, 57:327 (1988).

Ronald W. Ellis, Vaccine Development: Progression From Target Antigen to Product, *Adv. Exp. Med. Biol.*, 327:263 (1992).

Ferguson et al., Cell–Surface Anchoring Of Proteins Via Glycosyl–Phosphatidylinositol Stuctures, *Ann. Rev. Biochem.*, 57:285 (1988).

Freedman et al., B–Cell Monoclonal Antibodies and Their Use in Clinical Oncology, *Cancer Invest.*, 9:69 (1991).

Fynan, et al., DNA Vaccines: A Novel Approach to Immunization, *Int. J. Immunopharm.*, 17:79 (1995).

Galaktionow et al., Specific Activation of cdc25 Tyrosine Phosphatases by B–Tube Cyclins: Evidence for Multiple Roles of Mitotic Cyclins *Cell* 67:1181 (1991).

Harris et al., Gene Therapy for Cancer Using Tumour–Specific prodrug Activation, *Gene Ther.*, 1:170 (1994).

Hawkins et al., A Genetic Approach to Idiotypic Vaccination, *J. Immunother.*, 14:273 (1993).

Heard et al., Both Arabidopsis TATA (TBP) isoforms are functionally identical in RNA polymerase II and III transcription in plant cells: evidence for gene–specific changes in DNA binding specificity of TBP, *EMBO J.*, 12:3519 (1993).

Herber et al., Inductible Regulatory Elements in the Human Cyclin D1 promoter, *Oncogene*, 9, 1295 (1994).

Hoffman et al., Activation of the phosphatase activity of human cdc25A by a cdk2–cyclin E dependent phosphorylation at the $G_1$/S transition, *EMBO J.* 13:4302 (1994).

Honda et al., Dephosphorylation of human p34$^{cdc2}$ kinase on both Thr–14 and Tyr–15 by human cdc 25B phosphatase, *FEBS Lett.* 318:331 (1993).

Hoogenboom et al., Building Antibodies form their genes Rev. Fr. Transfus. Hemobiol. 36:19 (1993).

Hoogenboom et al., Construction and Expression of Antibody–Tumor Necrosis Factor Fusion Proteins *Mol. Immunol.*, 28:1027 (1991).

(List continued on next page.)

*Primary Examiner*—Robert A. Schwartzman
*Attorney, Agent, or Firm*—Foley & Lardner

[57] ABSTRACT

The invention provides the promoter of the cdc25B gene, a process for finding cdc25B promoters and methods for using the promoters for preparing a pharmaceutical.

43 Claims, 8 Drawing Sheets

OTHER PUBLICATIONS

Huang et al., A Novel Hepatitis B Virus (HBV) Genetic Element with Rev Response Element–Like Properties That Is Essential for Expression of HBV Gene Products, *Mol. Cell Biol.,* 13:7476 (1993).

Hughes et al., Monoclonal Antibody Targeting of Liposomes to Mouse Lung in vivo, *Cancer Res.,* 49:6214 (1989).

Huston et al., Medical Applications of Single–Chain Antibodies, *Intern. Rev. Immunol.,* 10:195 (1993).

Jinno et al., Cdc 25A is a novel phosphatase functioning early in the cell cycle, *EMBO J.* 13:1549.

Kakizuka et al., A mouse cdc25 homolog is differentially and developmentally expressed. *Genes Deve.* 6; 6:587.

Kaufman et al., Improved Vectors for Stable Expression of Foreign Genes in Mammalian Cells By Use of the Untranslated Leader Sequence from EMC Virus, *Nucl. Acids Res.,* 19:4485 (1991).

Kozak et al., The Scanning Model for Translation: An Update, *J. Cell Biol.,* 108:299 (1989).

Kristensen, Jorgen Scholer, Immunophenotyping in Acute Leukaemia, Myelodysplasitc Syndromes and Hairy Cell Leukaemia, *Danish Medical Bulletin,* 41:52 (1994).

Nicholas B La Thangue, DP and E2F Proteins: Components of a Heterodimeric Transcription Factor Implicated in Cell Cycle Control, Curr. Opin. *Cell Biol.,* 6:443 (1994).

Lee et al., Cloning of the GATA–binding Protein That Regulates Endothelin–1 Gene Expression in Endothelial Cells, *J. Biol. Chem.* 266:16188 (1991).

Lichtenstein et al., Definition and Functional Analysis of the Signal/Anchor Domain of the Human Respiratory Syncytial Virus Glycoprotein G, *J. Gen. Virol.,* 77:109 (1996).

Liu et al., Cell cycle–regulated repression of B–myb transcription: cooperation of an E2F site with a contiguous corepressor element; Nucleic Acids Res 24:2905 (1996).

Lucibello et al., Periodic cdc25C transcription is mediated by a novel cell cycle–regulated repressor element (CDE) *EMBO J.* 14:132 (1995).

MacLachlan et al., Cyclins, Cyclin–Dependent Kinases and Cdk Inhibitors: Implications in Cell Cycle Control and Cancer; *Crit. Rev. Eukaryotic Gene Expr.,* 5:127 (1995).

Maddon et al., The Isolation and Nucleotide Sequence of a CDNA Encoding the T Cell Surface Protein T4: A New Member of the Immunoglobulin Gene Family, *Cell* 42:93 (1985).

Malim et al., The HIV–1 rev trans–activator acts through a structured target sequence to activate nuclear export of unspliced viral mRNA, *Nature,* 338:254 (1989).

Malcolm A.S. Moore, Hematopoietic Reconstruction New Approaches, *Clin. Cancer Res.,* 1:3 (1995).

Morgan et al., Retroviral vectors containing putative internal ribosome entry sites: development of a polycistronic gene transfer system and applications to human gene therapy, *Nucl. Acids Res.,* 20:1293 (1992).

Craig A. Mullen, Metabolic Suicide Genes in Gene Therapy, *Pharmac. Ther.,* 63:199 (1994).

Farmarz Naeim, Selection of Monoclonal Antibodies in the Diagnosis and Classification of Leukemias, Dis. Markers, 7:1 (1989).

Okazaki et al. Isolation of cDNA encoding the Xenopus homologue of mammalian Cdc25A that can induce meiotic maturation of oocytes, *Gene* 178:111 (1994).

Oshima et al., Cloning sequencing and expression of cDNA for human B–glucuronidase, *Proc. Natl. Acad. Sci. USA* 84:685 (1987).

Pauli et al., Organ–preference of metastasis, *Cancer Metast. Rev.,* 9:175 (1990).

Pelletier et al., Internal initiation of translation of eukaryotic mRNA directed by a sequence derived from poliovirus RNA, *Nature,* 324:320 (1988).

Perlmutter et al., Structure and Expression of lck Transcripts in Human Lymphoid Cells, *J. Cell.* 38:117 (1988).

Pusztai et al., Growth Factors: Regulation of Normal and Neoplastic Growth, *J. Pathol.* 169:191 (1993).

Ratner et al., Complete nucleotide sequence of the AIDS virus, HTLV–III, *Nature,* 313:277 (1985).

Riechmann et al., Reshaping human antibodies for therapy, *Nature,* 332:323 (1988).

Schranz et al., Monoclonal Antibodies: New Diagnostic and Therapeutic Means in Acute Leukaemias, *Therapia Hungarica,* 38:3 (1990).

Schrewe et al., Cloning of the Complete Gene for Carcinoembryonic Antigen: Analysis of Its Promoter Indicates a Region Conveying Cell Type–Specific Expression, *Mol. Cell Biol.,* 10:2738 (1990).

Semenza et al., Hypoxia–indicible nuclear factors bind to an enhancer element located 3' to the human erythropoietin gene. *Proc. Nat'l Acad. Sci.* 88:5680 (1991).

Sedlacek et al., Antibodies as Carriers of Cytotoxicity, *Contrib. to Oncol.,* 32, Karger Verlag, Munich (1988).

Sedlacek et al., Monoclonal Antibodies in Tumor Therapy, *Contrib. to Oncol.,* Karger Verlag, Munich (1992). 114–133, 42–85.

Shaw et al., The lck Tyrosine Protein Kinase Interacts with the Cytoplamic Tail of the CD4 Glycoprotein through its Unique Amino–Terminal Domain, *Cell,* 59:627 (1989).

Stickney et al., Biologic response modifiers: therapeutic approaches to lymphoproliferative diseases, *Curr. Opin. Oncol.,* 4:847 (1992).

Strubin and Struhl et al., Yeast and Human TFIID with Altered DNA–Binding Specificity for TATA Elements, *Cell,* 68:721 (1992).

Sugitomo et al., Efficient Expression of Drug–selectable Genes in Retroviral Vectors Under Control of an Internal Ribosome Entry Site, *BioTech.,* 12:694 (1994).

Triezenberg, Structure and function of transcriptional activation domains, *Curr. Opin. Gen. Developm.,* 5:190 (1995).

Triezenberg, Functional dissection of VP16, the transactivator of herpes simplex virus immediate early gene expression, *Genes Develom.,* 2:718 (1988).

Truss et al., Steroid Hormone Receptors: Interaction with Doxyribonucleic Acid and Transcription Factors, *Endorcr. Rev.* 14:459 (1993).

Turner et al., Interaction of the Unique N–Terminal Region of Tyrosine Kinase p56$^{lck}$ with Cytoplasmic Domains *Cell.,* 60:755 (1990).

Van Kooten et al., Cytokines and intracellular Signals Involved in the Regulation of B–CLL Proliferation, Leukemia Lymphoma 12:27 (1993).

Varner et al., Review: The Integrin $a_vB_3$: Angiogenesis and Apoptosis, *Cell Adh. Commun.,* 3:367 (1995).

Vijaya et al., Transport to the Cell Surface of a Peptide Sequence Attached to the Truncated C Terminus of an N–Terminally Anchored Integral Membrand Protein, *Mol. Cell Biol.,* 8:1709 (1988).

Westerink et al., Anti–idiotypic antibodies as vaccines against carbohydrate antigens, Springer Seminars in Immunopathol., 15:227 (1993).

Wilson et al., A Nonerythroid GATA–Binding Protein Is Required for Function of The Human Preproendothelin–1 Promoter in Endothelial Cells, *Mol. Cell Biol.,* 10:4854 (1990).

Winter et al., Man–made antibodies, *Nature,* 349:293 (1991).

Zwicker et al., Cell cycle regulation on cdc25C transcription is mediated by the periodic repression of the glutamine–rich activitors NF–Y and Sp1, *Nucl Acids Res.* 23:3822 (1995).

Zwicker et al., Cell cycle regulation of the cyclin A, cdc25C and cdc2 genes is based on a common mechanism of transcriptional repression, *EMBO J..* 14:4514 (1995).

Zwicker et al. Cell cycle–regulated transcription in mammalian cells, *Progr. Cell Cycle Res.,* 1:91 (1995).

Zwicker et al. Cell–cycle regulation of gene expression by transcriptional repression, *TiGS* 14:3 (1997).

Activator-responsive promoter unit

FIG. 5
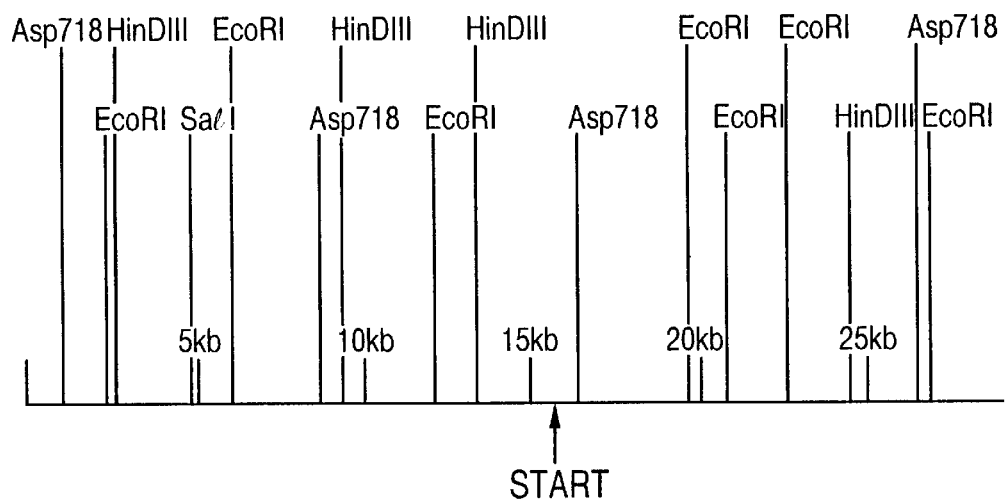
a)
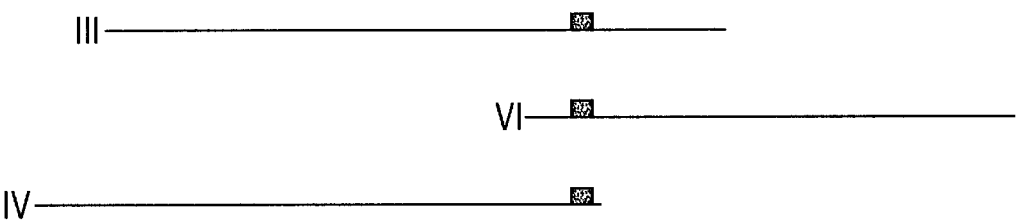
b)
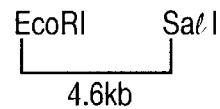

FIG. 7  Table 1 (SEQ ID NO.: 7)

|  |  | E Box |  |
|---|---|---|---|
| -952 | AGTTCT<u>CAAC</u> | <u>TG</u>CCCACTAG | GTCCTTCCCA |
| -922 | GCTCATTCCA | GGAAAACAGA | CTCAGCTGCA |
| -892 | AGGTGATTAG | GTCATTAGAA | AACGCTCATT |
| -862 | GTAAACTAAT | AGCAAATTCA | GCCTCTTTCA |
| -832 | CCTTCAAAGA | AACACTAAAT | ATGGTGCTAT |
| -802 | TAACCCCAAA | TTAGCCAAGT | GGGTGTGAGA |
| -772 | TTTTTTTCCC | CCTAGTTGGG | TTCTCTGGTG |
|  |  | E Box |  |
| -742 | GCATGTCC<u>CA</u> | <u>ACTG</u>TGTGTT | GCAGAAATCA |
| -712 | TTGCCTAAAT | CTAAGCGTCT | AATTCTCAGG |
| -682 | AGAATAGGCT | CAGTGGGGTC | ACATCTAAAC |
| -652 | TCTGGTGCCC | CAGAACCCAG | CAGTTCCACT |
| -622 | GTGCCTCGCA | AAGGGCTGCC | AGCAAACGAC |
| -592 | TGCAGCTGCT | CTGTGAGGTC | CAGGGGCGAT |
| -562 | GACAGGAGGC | TGCACCATCA | GCGGAGTCCC |
| -532 | TGAGGGAGCT | TCTATGTCTC | TGCCACTCAA |
| -502 | CCGAACCTGT | GACCTTAAAC | GAGTTAAAGA |
| -472 | GCTTTTCAAC | GCTGGGGTCT | GTGAACTGGA |
| -442 | CAGGGAACGC | AGTGCTCACA | GCATACTTGG |
| -412 | CAAACGTCCT | GGGCTCAAGC | AGAGCGTCGC |
| -382 | ACCGTCCCTT | ACTGATGAAC | GTGCATGATG |
| -352 | GTAAACGTTG | AGGGCTCCTT | ATGAGGCCAC |
| -322 | CTTAGGGGAT | GACTACTCCC | TCTGAGGGTA |
| -292 | GAGGGCTGCT | CCCACCTCCA | AACCCTGTTC |
| -262 | CAGGAGGCAA | TATCCTGGAG | GCCCAGGATT |
|  | E2F |  | SP1 |
| -232 | <u>CTCGCG</u>TCAA | TGGGAGC<u>GGG</u> | <u>CGGGGCCGGG</u> |
|  | SP1 |  |  |
| -202 | <u>GCGGT</u>ACGTG | TGGGGCAGGG | GGTTAACCCA |

FIG. 7 CONTINUED

```
-172    ACTCCCCGAG    TCACCCTAAG    AAGCCAGGCG

-142    AGCAGAAGTA    GCTGGTCCAG    CCTCAGCCTC

SP1                   SP1
-112    AGCCCCGCCC    TTGGTCCCGC    CCTCCCGGAA

NF-Y                  E2F
-82     CCGGCGCCCC    CATTGGTGGC    GTCTGGCGGC

TATA
-52     GCTGCCGCTG    TTATTTTTCG    AATATATAAG

+1
-22     GAGGTGGAGG    TGGCAGCTGC    CCAGCTCGGC

+9      GTCCTCCCT     CCCTTCCTCC    CCACATCCCT

+39     CTCCTCACTC    CCAGGCCCAT    TGCTCTTCCT published cDNA start

+69     CCCTCCCTTC    CCTCCCTCCT    TCCCCTCACC

+99     CCAGGCTCAC    TCTCGGAGCT    GAGCCAGCTG

+129    GGTCGGCGTC    TGCTGGCCGC    TGTACTGTGG

+159    CCCTCTAGCT    AG
```

FIG. 8

Table 2a

| a Construct | b Growing cells | c Serum-deprived cells | d Cell cycle induction |
|---|---|---|---|
| B-950 | 100 | 9.9 | 10.1 |
| B-340 | 153.8 | 25.1 | 6.1 |
| B-180 | 121.3 | 18.0 | 6.8 |
| B-100 | 76.7 | 10.1 | 6.8 |
| B-80 | 29.9 | 8.5 | 3.5 |
| B-20 | 22.5 | 15.7 | 1.4 |
| B-950 m TATA | 72.5 | 9.0 | 7.7 | m = mutated

FIG. 9

Table 2b

| a) | b) | c) | d) |
|---|---|---|---|
| B-223 | 100 | 11.4 | 8.8 |
| B-209 | 87.5 | 11.7 | 7.5 |
| B-180 | 58.8 | 10.6 | 5.5 |
| B-100 | 28.0 | 5.0 | 5.6 |
| B-87 | 25.3 | 6.0 | 4.2 |
| B-67 | 22.0 | 8.4 | 2.6 |
| B-223mY | 26.6 | 7.0 | 3.8 |

PROMOTER OF THE CDC25B GENE, ITS PREPARATION AND USE

FIELD OF THE INVENTION

The invention relates to the promoter of the cdc25B gene, to a process for finding cdc25B promoters, and to the use of the cdc25B promoter for preparing a pharmaceutical.

BACKGROUND OF THE INVENTION

Cell division is subdivided into the consecutive phases $G_0$ or $G_1$, S, $G_2$ and M. The S phase is the DNA synthesis phase; it is followed by the transition phase $G_2$ ($G_2$ phase), which is followed in turn by the mitosis phase (M phase), in which the parent cell divides into two daughter cells. The resting phase $G_0$ ($G_0$ phase) or the transition phase $G_1$ ($G_1$ phase) is located between M phase and the S phase.

Cell division is driven forward by a group of protein kinases, i.e. the cyclin/cdk complexes. These comprise a catalytic subunit, known as a cyclin dependent kinase (cdk), for example cdk1, -2, -3, -4, -5, -6, -7 or -8) and a regulatory subunit, i.e. cyclin, for example cyclin A, -B1-B3, -D1-D3, -E, -H, or -C.

Different cdk complexes are particularly active in each phase of the cell cycle. Thus, for example, the cdk complexes cdk4/cyclin D1-3 and cdk6/cyclin D1-3 are active in the mid $G_1$ phase, the cdk complex cdk2/cyclin E is active in the late $G_1$ phase, the cdk complex cdk2/cyclin A is active in the S phase, and the cdk complexes cdk1/cyclin B1-3 and cdk1/cyclin A are active in the $G_2$/M transition phase.

The cyclin/cdk complexes act by phosphorylating, and consequently activating or inactivating, proteins that are directly or indirectly involved in regulating DNA synthesis and mitosis. In accordance with their function in the cell cycle, the genes for some cyclins and cdk's are periodically transcribed and/or periodically activated or inhibited, for example by controlled degradation of cyclins, by cell cycle phase-specific binding of inhibitors (e.g. p16INK4A, p15INK4B, p21Cip1, P27Kip1, p18INK4C, p19INK4D and P57) or by modification by activating (e.g. cdc25 phosphatases or cdk7/cyclin H) or inhibiting (e.g. weel kinase) enzymes (reviews in Zwicker et al., *Progr. Cell Cycle Res.*, 1:91 (1995); La Thangue, *Curr. Opin. Cell Biol.*, 6:443 (1994); MacLachlan et al., *Crit. Rev. Eukaryotic Gene Expr.*, 5:127 (1995)).

Higher eukaryotes possess at least three cdc25 phosphatases, namely cdc25A, cdc25B and cdc25C. cDNAs encoding these phosphatases already have been cloned and analyzed (Okazaki et al., Gene 178:111 (1996); Galaktionow et al., *Cell* 67:1181 (1991)). All three phosphatases appear periodically in the cell cycle. However, the activating functions of these cdc25 phosphatases evidently are different (Jinno et al., *EMBO J.* 13:1549 (1994); Honda et al., *FEBS Lett.* 318:331 (1993); Hoffmann et al., *EMBO J.* 13:4302 (1994)).

cdc25A is predominantly expressed in late $G_1$ phase, and in particular regulates the transition from $G_1$ to S phase (start of cell cycle) by activating cdk/cyclin complexes; it is itself regulated by Myc (transcription) and Raf (activity). cdc25B dephosphorylates the tyrosines (tyrosine 14 and tyrosine 15) in the ATP-binding pocket of cdk1, thereby leading to their activation; furthermore, it can be stimulated by cyclin B (1–3) independently of cdk1, and its expression is deregulated and augmented in virus (SV40 or HPV)-infected cells. cdc25C also dephosphorylates the tyrosines (tyrosine 14 and tyrosine 15) in the ATP-binding pocket of cdk1, leading to their activation; it is expressed, in particular, in $G_2$ phase, and regulates entry into M phase.

Periodic expression of cdc25C in the $G_2$ phase of the cell cycle essentially is regulated by an element (CDE-CHR) in the promoter region of cdc25C; that element is occupied by a repressor protein in $G_0/G_1$ phase and is free in $G_2$ phase. While the nucleotide sequence of this promoter element has been identified and also has been found in the promoters of the cyclin A and cdk1 genes, a somewhat different nucleotide sequence (E2FBS-CHR) has been detected in the promoter for Bmyb. Investigation of the cell cycle-dependent function of these promoter elements has shown that their blockade in the $G_0/G_1$ phase is followed by upregulation of the transcription of the relevant gene, where upregulation takes place particularly early (in the mid $G_1$ phase) for the B-myb gene, in the $G_1$/S transition phase for the cyclin A, in the S phase for the cdk1 gene, and only in the late S phase for the cdc25C gene (Zwicker et al., *Progress in Cell Cycle Res.* 1:91 (1995); Lucibello et al., *EMBO J.* 14:132 (1995); Liu et al., *Nucl. Acids Res.* 24:2905 (1995); Zwicker et al., *Nucl. Acids Res.* 23:3822 (1995); *EMBO J.* 14:4514 (1995)).

In addition, it has been found that the CDE-CHR element of the promoter for cyclin 25C, cyclin A and the cdk1 gene, and the E2FBS-CHR element of the promoter for the B-myb gene are not only able to inhibit activation and transcription of the homologous genes in the $G_0/G_1$ phase, but also are able to inhibit the activation and transcription of other genes. See, for example, WO96/06943, DE19605274.2, DE19617851.7, WO96/06940, WO96/06938, WO96/06941 and WO96/06939.

Those applications disclose preparation of a chimeric promoter, by combining a cell cycle-dependent promoter with a nonspecific, cell-specific, virus-specific or metabolically activatable promoter. This allows for regulated activation of transcription of an effector gene that encodes a protein for the prophylaxis and/or therapy of a disease. Such diseases may, for example, be tumor diseases, leukemias, autoimmune diseases, arthritides, allergies, inflammations, rejection of transplanted organs, diseases of the blood circulatory system or the blood coagulation system, or infections of, or damage to, the central nervous system.

The chimeric promoter is a particular example of this possibility of combining different promoters with a cell cycle-specific promoter element. In the chimeric promoter, the activity of a nonspecific, cell-specific, virus-specific or metabolically activatable activation sequence (or promoter sequence) is to a large extent restricted to the S and $G_2$ phases of the cell cycle by the CDE-CHR or E2FBS-CHR promoter element which immediately adjoins it downstream.

Subsequent investigations on the mode of function of the CDE-CHR promoter element, in particular, revealed that the cell cycle-dependent regulation by the CDE-CHR element of an upstream activator sequence is to a large extent dependent on whether the activation sequence is activated by transcription factors having glutamine-rich activation domains (Zwicker et al., *Nucl. Acids Res.* 23:3822 (1995)). Examples of these transcription factors are Sp1 and NF-Y.

As a consequence, this restricts the use of the CDE-CHR promoter element for chimeric promoters. The same must be assumed to be true for the E2F-BS-CHB promoter element of the B-myb gene (Zwicker et al., *Nucl. Acids Res.* 23:3822 (1995)).

SUMMARY OF THE INVENTION

It is therefore an object of the present invention to provide cell cycle-specific promoters and promoter elements whose $G_0$-specific and $G_1$-specific repression is dependent on circumstances other than those to which the CDE-CHR promoter element is subject.

It is a further object of the present invention to provide methods for identifying such promoters.

It is a still further object of the present invention to provide nucleic acid constructs comprising such promoters.

It is yet another object of the invention to provide nucleic acid constructs comprising such promoters and at least one structural gene.

It is a further object of the invention to provide nucleic acid constructs comprising such promoters combined with at least one further activation sequence.

In achieving these objects, there has been provided, in accordance with one aspect of the present invention, a promoter of the cdc25B gene, which comprises a sequence which hybridizes under stringent conditions with a sequence as depicted in Table 1 (SEQ ID NO: 7) or a functional part thereof.

In one embodiment, the promoter comprises the sequence depicted in Table 1 (SEQ ID NO: 7) or a functional part thereof. In another embodiment, the functional part of the promoter comprises the TATA box, at least one Sp1-binding site and at least one NFY-binding site. In yet another embodiment, the promoter further comprises at least one E2F-binding site. In a further embodiment, the promoter further comprises at least one E box.

In a preferred embodiment, the promoter comprises the sequence encompassing the nucleotides from approx. −950 to approx. +167 of Table 1(SEQ ID NO: 7), or about −950 to about +3, or about −930 to about +3, or about −720 to about +3, or about −340 to about 3, or about −180 to about +3, or about −100 to about +3, or about −80 to about +3, or about −60 to about +3, or about −30 to about +3, or fragments thereof which still comprise all the functional cis-regulatory elements of the promoter sequence of the nucleotides from about −950 to about +167, or from about −950 to about +3, or from about −930 to about +3, or from about −720 to about +3, or from about −340 to about 3, or from about −180 to about +3, or from about −100 to about +3, or from about −80 to about +3, or from about −60 to about +3, or from about −30 to about +3, as depicted in FIG. 6.

In accordance with another aspect of the present invention, there has been provided a method for identifying cdc25B promoters, by using a labeled cdc25B promoter or a labeled promoter sequence which hybridizes under stringent conditions with a sequence as depicted in Table 1 (SEQ ID NO: 7) or a functional part thereof, to screen a genomic DNA library, wherein the screening is carried out using hybridization under stringent conditions. In one embodiment, the genomic library is from mammalian cells.

In accordance with another aspect of the present invention, there has been provided a method for isolating the murine cdc25B promoter, comprising screening a murine genomic phage library, obtained from the mouse strain 129FVJ, with a probe comprising a part of the sequence depicted in Table 1 (SEQ ID NO: 7). In one embodiment, the probe comprises sequence SEQ ID NO.: 4.

In accordance with still another aspect of the invention, there has been provided a nucleic acid construct comprising a promoter of the cdc25B gene, which comprises a sequence which hybridizes under stringent conditions with a sequence as depicted in Table 1 (SEQ ID NO: 7) or a functional part thereof.

In one embodiment, the nucleic acid construct further comprises a structural gene. In another embodiment, the promoter is upstream of the structural gene. In another embodiment, the 5' noncoding region of the cdc25B gene (SEQ. ID. NO: 7) comprising the nucleotide sequence from +1 to about +167 is inserted between the promoter and the structural gene.

In accordance with yet another aspect of the invention, the promoter in the nucleic acid construct is combined with at least one further activation sequence, where the further activation sequence is selected from the group consisting of non-specific, virus-specific, metabolically specific, cell-specific, cell cycle-specific and cell proliferation-dependent activation sequences. In one embodiment, the further activation sequence is selected from the group consisting of promoters which are activated in endothelial cells, peritoneal cells, pleural cells, epithelial cells of the skin, cells of the lung, cells of the gastrointestinal tract, cells of the kidney and urine-draining pathways, muscle cells, connective tissue cells, hematopoietic cells, macrophages, lymphocytes, leukemia cells, tumor cells and gliacells; viral promoter sequences; promoter or enhancer sequences which are activated by hypoxia, cell cycle-specific activation sequences of the genes encoding cdc25C, cyclin A, cdc2, E2F-1, B-myb and DHFR, and binding sequences for transcription factors which appear or are activated in a cell proliferation-dependent manner.

In accordance with another aspect of the invention, the promoter comprises at least one mutated transcription factor binding site. In one embodiment, the mutation is in the TATA box.

In accordance with still another aspect of the invention, the nucleic acid construct comprises a mutated promoter as set forth above and further comprises (a) a first structural gene and (b) an additional promoter or enhancer sequence which activates the transcription of at least one second structural gene, where the second structural gene encodes a transcription factor that activates the mutated promoter, and where activation of the mutated promoter occurs via at least one mechanism selected from the group consisting of non-specific activation, cell-specific activation, virus-specific activation, tetracycline activation, and cell cycle-specific activation. In a particular embodiment, the transcription factor binds to a mutated TATA box.

In accordance with yet another aspect of the invention, there has been provided a nucleic acid construct comprising in the orientation from 3' to 5': (a) a cdc25B promoter as set forth above, where the promoter comprises a TATA box that is mutated to TGTA, (b) the sequence GCCACC, (c) the cDNA for an immunoglobulin signal peptide, (d) a cDNA encoding β-glucuronidase, (e) the promoter of the vWF gene, and (f) the cDNA for a TATA box-binding protein.

In one embodiment, the signal peptide cDNA comprises nucleotides 63 to 107 of the immunoglobulin signal peptide (SEQ ID NO: 11), the glucuronidase cDNA comprises nucleotides 93 to 1982 of the glucuronidase cDNA (SEQ ID NO: 12), the vWF gene promoter comprises nucleotides −487 to +247 of the vWF gene promoter (SEQ ID NO: 13) and the TATA box-binding protein cDNA comprises nucleotides 1 to 1001 of the TATA box-binding protein, which is mutated by replacing A with T at nucleic acid position 862, by replacing GT with AC at positions 889 and 890, and by replacing C with G at position 895.

In another embodiment, the nucleic acid construct comprises a promoter and a structural gene, further comprising at the 3' end (a) a nuclear retention signal, and (b) an additional promoter which activates transcription of a gene encoding a nuclear export factor, where the nuclear export factor binds to the nuclear retention signal mRNA, and where at least one of the promoters is a cdc25B promoter as set forth above.

In yet another embodiment, at least one promoter or enhancer is replaced with an activator-responsive promoter unit. In a particular embodiment, the activator-responsive promoter unit comprises: (1) at least one activator subunit whose basal transcription is activated by a promoter or enhancer, and (2) an activator-responsive promoter which is activated by the expression product of the activator subunit.

In a further embodiment, the activator subunit comprises: (a) a promoter of the cdc25B gene comprising a sequence which hybridizes under stringent conditions with a sequence as depicted in Table 1 (SEQ ID NO: 7), (b) the SV40 nuclear localization signal PKKKRKV (SEQ ID NO: 9), (c) amino acids 406 to 488 of the HSV-1 VP16 acid transactivating domain (SEQ ID NO: 14), and (d) a cDNA encoding amino acids 397–435 of the cytoplasmic portion of the CD4 glycoprotein (SEQ ID NO: 15), and further comprising a second activator subunit, where the second activator subunit comprises: (e) nucleic acids −290 to +121 of the promoter of the cdc25C gene (SEQ ID NO: 9), (f) the SV40 nuclear localization signal PKKKRKV(SEQ. ID. NO: 9), (g) amino acids 1 to 147 of the cDNA for the DNA-binding domain of the Gal4 protein (SEQ ID NO: 16) and (h) amino acids 1–71 of the cDNA for the CD4-binding sequence of the p56 lck protein (SEQ ID NO: 17), and where the nucleic acid construct further comprises (g) up to about 10 copies of the activator-responsive promoter, where the activator-responsive promoter comprises (SEQ ID NO: 8) (i) the 5'-CGGACAATGTTGACCG-3' binding sequence for Gal4 binding protein and (ii) nucleotides 48 to 5191 of the basal SV40 promoter (SEQ ID NO: 18).

In accordance with another aspect of the invention there is provided a nucleic acid construct as set forth above, further comprising a structural gene which encodes (a) an active compound, (b) an enzyme or (c) a fusion protein which is composed of a ligand and an active compound or a ligand and an enzyme. In one embodiment, the structural gene encodes an active compound selected from the group consisting of enzymes, fusion proteins, cytokines, chemokines, growth factors, receptors for cytokines, receptors for chemokines, receptors for growth factors, peptides and proteins having an antiproliferative or cytostatic or apoptotic effect, antibodies, antibody fragments, angiogenesis inhibitors, peptide hormones, coagulation factors, coagulation inhibitors, fibrinolytic proteins, peptides and proteins having an effect on blood circulation, blood plasma proteins, antigens of infectious agents, antigens of cells, antigens of tumors, thrombosis-inducing substances, complement-activating proteins, virus coat proteins and ribozymes.

In another embodiment, the nucleic acid construct encodes an enzyme which cleaves a precursor of a drug into a drug. In yet another embodiments, the structural gene encodes a ligand/active compound fusion protein or a ligand/enzyme fusion protein, where the ligand is selected from the group consisting of cytokines, growth factors, antibodies, antibody fragments, peptide hormones, mediators and cell adhesion proteins.

In one embodiment, the nucleic acid is DNA. In another embodiment, the nucleic acid construct is inserted into a vector. In yet another embodiment, the vector is a plasmid vector or a viral vector.

In accordance with a still further aspect of the invention, there is provided a method for preparing a nucleic acid construct, comprising inserting a promoter as set forth above into a vector.

In accordance with yet another aspect of the invention, there is provided a host cell comprising a nucleic acid construct as set forth above. In a particular embodiment, the host cell is an endothelial cell.

In accordance with one other aspect of the invention, there is provided a method of treating a disease selected from the group consisting of tumor diseases, leukemias, autoimmune diseases, allergies, arthritides, inflammations, organ rejections, graft versus host reactions, blood coagulation diseases, circulatory diseases, anemia, infections, hormone diseases and CNS damage, comprising administering to a patient in need thereof a pharmaceutical comprising a nucleic acid construct itself as set forth above, or a host cell comprising the nucleic acid construct, or a protein or polypeptide prepared using the nucleic acid construct.

BRIEF DESCRIPTION OF THE FIGURES

FIGS. 5A–5B: Genomic structure of the murine cdc25B promotor/enhancer region. By carrying out restriction digestion with various enzymes, a map of the genomic locus was prepared from the three phage clones isolated. A 4.6 kb fragment directly bordering on the 5' region of the cDNA was excised from phage VI and subcloned into the Bluescript SKII vector (Stratagene).

a)=phage clone b)=subcloned fragment

Figure 6:
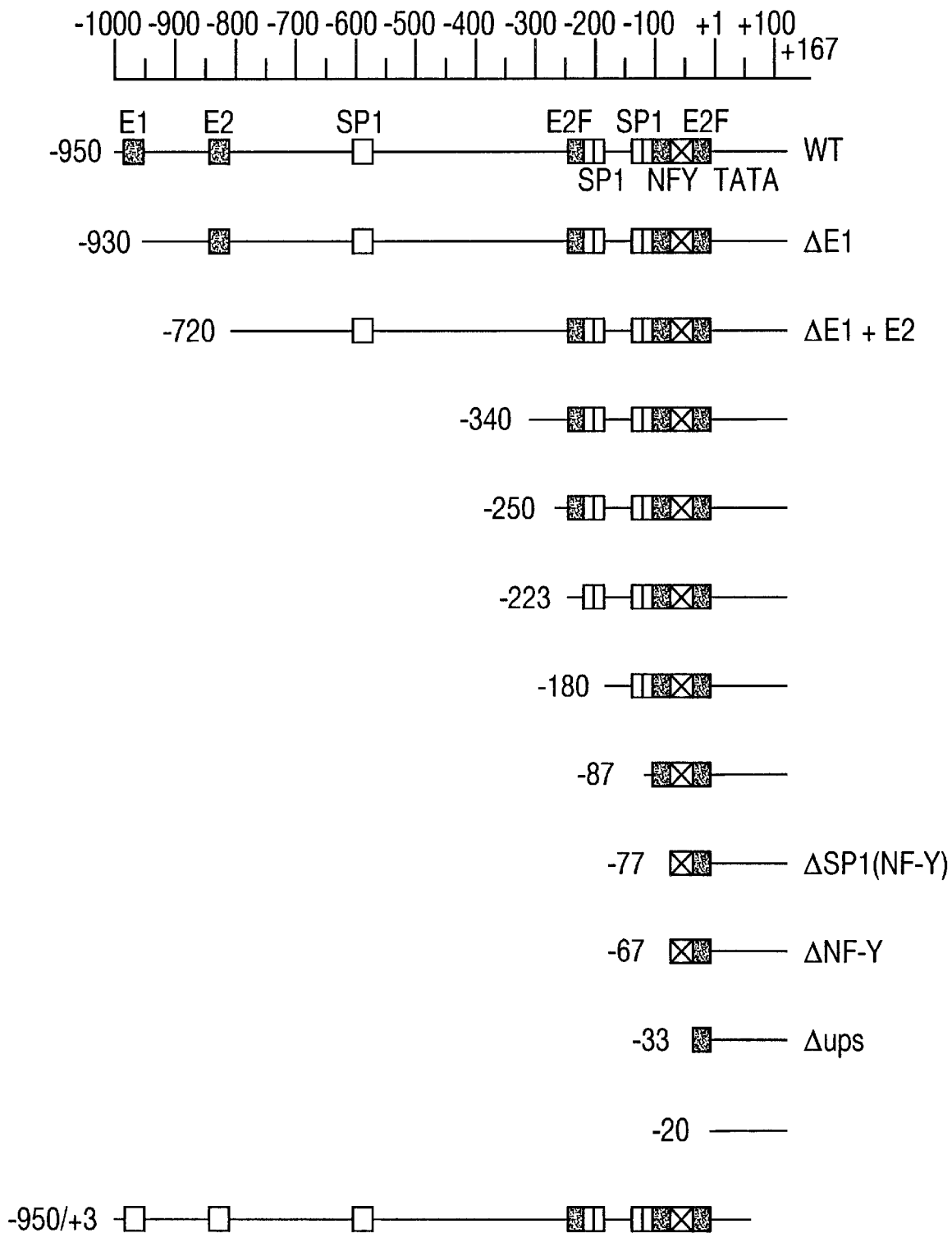

FIG. 6: Deletion mutants of the murine cdc25B promoter. The figure depicts different 5' deletions and a 3' deletion of the promoter, and the putative transcription factor-binding sites which are located in this region of the promoter. The designation of the individual deletion constructs is based on the position of the 5' end in the sequence. The fragments were purified through QIAquickTM spin columns (Qiagen) and cloned into the pGL3 vector (Promega).

FIG. 7: Shows in Table 1 the sequenced region of the murine cdc25B promoter. The region which directly adjoins the 5' end of the published cDNA sequence (Kakizuka et al., Genes Dev. 6:587 (1992)) was sequenced. The table shows the arrangement of the putative binding sites and the transcription start. The putative binding sites are, on the one hand, activators such as those which occur in many cell cycle-specific promoters which are regulated by repression. Putative E2F-binding sites are observed, together with, in the 5' region, two E boxes to which repressor activity is attached. The TATA box which is depicted is a sequence element which is unusual for genes which are regulated in a cell cycle-specific manner and which is evidently functionally important in this promoter since its specifies the position of the transcription start.

FIG. 8: Shows the promoter activity of the different deletion constructs. Table 2a shows the relative luciferase activity in growing and serum-deprived NIH-3T3 cells of some of the constructs depicted in FIG. 6. The cell cycle induction of the promoter, which is determined from the quotient of the values for growing versus starved cells is given in the final column. The value for the longest construct in growing cells is set at 100, and the remaining values are compared with this reference value. The deletions shown in Table 2a the are of relatively large size for determining functional regions in the promoter, and point mutation of the TATA box.

FIG. 9: Shows in Table 2b the activities of other constructs shown in FIG. 6. These data show the effects on activity of sequential deletion of the proximal Sp1-binding site and the NF-Y-binding site, and point mutation of the NF-Y-binding site. Activity in growing cells of the construct containing all these activator-binding sites is arbitrarily set at 100 (the actual activity does not correspond to that of construct B-950).

a) Tested deletion constructs (see FIG. 6)

b) Promoter activity in growing cells c) Promoter activity in resting (serum-deprived) cells d) Cell cycle induction (the quotient of the promoter activity in growing cells as compared with that in resting cells).

DETAILED DESCRIPTION

Analysis of the nucleotide sequence of the promoter of the murine cdc25B gene, and the nucleotide sequence of the immediately downstream 5'-noncoding region, including the initiation (or start) region of the cdc25B gene (SEQ ID NO: 7) (nucleotide sequence −950 to +167) showed that the functional regions of the cdc25B promoter sequence contain two E boxes, two (putative) E2F-binding sites, four (putative) Sp1-binding sites, one (putative) NF-Y-binding site and a TATA box. Surprisingly, it was not possible to find any nucleotide sequences having homology with CDE-CHR or E2FBS-CHR. Consequently, the functional regions of the cdc25B promoter sequence are clearly different from any of the functional regions of the promoters of the cdc25C, cyclin A, cdk1 or B-myb genes. It also is surprising that until the present invention there have been no reports of a cell-cycle gene promoter containing a functional TATA box.

The present invention therefore provides the promoter of the cdc25B gene, which promoter contains a sequence which hybridizes, under stringent conditions, with a sequence as depicted in Table 1 (SEQ ID NO: 7) or a functional part thereof, in particular to the promoter having the sequence depicted in Table 1 (SEQ ID NO: 7) or a functional part thereof.

The entire sequence, or fragments, of the cdc25B promoter were cloned into a plasmid upstream of a luciferase gene, and these plasmids were transfected into mouse or human resting and proliferating fibroblasts and the quantity of luciferase expressed was measured.

It was found that (in contrast to the situation in proliferating cells) the cloned cdc25B sequence (SEQ ID NO: 7) (promoter and 5'-noncoding region; approx. −950 to approx. +167) led to strong suppression of luciferase gene expression in resting cells, with this suppression being reduced in a stepwise manner by making deletions at the 5' end of the cdc25B promoter (SEQ ID NO: 7) (from approx. −950 to approx. +167 to approx. −30 to approx. +167). Deletion fragments smaller than approx. −180 to approx. +167 led to the promoter activity being reduced in proliferating cells as well.

It will be understood that, in the context of the present invention, functional parts of promoters include the transcription factor-binding sites detailed above, especially when they encompass more than approximately 50% of the entire promoter. Particular preference is given to functional parts containing the TATA box, at least one Sp1-binding site, at least one NFY-binding site and, where appropriate, at least one E2F-binding site and, where appropriate, at least one E box, such that it is possible to achieve cell cycle-dependent expression of an effector gene. These promoter sequences include, in particular, promoter sequences of the murine cdc25B gene; however, they also include promoter sequences of the human cdc25B gene.

Other preferred parts of the novel promoter are, according to Table 1 (SEQ ID NO: 7), the nucleotides from approx. −950 to approx. +167, from approx. −950 to approx. +3, from approx. −930 to approx. +3, from approx. −720 to approx. +3, from approx. −340 to approx. +3, from approx. −180 to approx. +3, from approx. −100 to approx. +3, from approx. −80 to approx. +3, from approx. −60 to approx. +3 or from approx. −30 to approx. +3, and also parts thereof, which contain the corresponding functional cis-regulatory elements in accordance with FIG. 6, in particular 5' deletions and/or 3' deletions.

The present invention provides a process for finding cdc25B promoters, by screening genomic DNA libraries, preferably from mammalian cells, with a novel promoter or part of a promoter. The promoter, or part of a promoter may be labeled, preferably radioactively labeled, and use to screen the genomic libraries by means of hybridization under stringent conditions. The preparation of genomic DNA libraries and hybridization under stringent conditions are well known to those skilled in the art. These techniques are described, for example, in Sambrook et. al. (1989) MOLECULAR CLONING A LABORATORY MANUAL, Cold Spring Harbor Laboratory, New York. See, for example, chapters 9–11, which are incorporated herein by reference. In particular pages 9.30–9.58 describe typical conditions for hybridization under stringent conditions, for example by hybridization at 68° in aqueous solution, for example in 6×SSC or 6×SSPE. Typical conditions include, for example, hybridization at 68° C. for 6–8 hours, or up to 20 hours, followed by washing in 2×SSC, 0.1% SDS, twice for 30 minutes at 55° C. and three times for 15 minutes at 60° C. The skilled artisan will recognize that alternative methods for hybridization under stringent conditions are well known in the art. Methods for optimizing hybridization conditions also are well known in the art, and are described, for example, by Szostak, et al. (1979) HYBRIDIZATION WITH SYNTHETIC OLIGONUCLEOTIDES, *Methods in Enzymol.* 68:419–482. For example, in order to isolate the murine cdc25B promoter, a murine genomic phage library, can be screened with a probe containing a portion of the sequence depicted in Table 1 (SEQ ID NO: 7), preferably one that contains the sequence SEQ ID NO: 4. Suitable murine genomic phage libraries are well known in the art and also are commercially available, for example, from the mouse strain 129 FVJ, (Stratagene, La Jolla, Calif.).

The present invention additionally provides a nucleic acid construct containing at least one novel promoter. Preferably, the novel promoter sequence of the cdc25B gene is combined with a structural gene, i.e. in general with a gene which encodes a protein or an RNA in the form of an active compound. In the simplest case, this combination can constitute a nucleic acid construct which contains the nucleotide sequence of the novel promoter for the cdc25B gene and a structural gene, with the promoter activating the transcription of the structural gene, preferably in a cell cycle-dependent manner. The novel promoter preferably is arranged upstream of the structural gene.

In another preferred embodiment, the 5'-noncoding region of the cdc25B gene (SEQ ID NO: 7) (nucleotide sequence from +1 to approx. +167) is inserted between the novel promoter and the structural gene.

In a further preferred embodiment, the novel promoter is combined with at least one further nonspecific, virus-specific, metabolically-specific, cell-specific, cell cycle-specific and/or cell proliferation-dependent activation sequence for the purpose of regulating the expression of a structural gene. Examples are:

- promoters that are activated in endothelial cells, peritoneal cells, pleural cells, epithelial cells of the skin, cells of the lung, cells of the gastrointestinal tract, cells of the kidney and urine-draining pathways, muscle cells, connective tissue cells, hematopoietic cells, macrophages, lymphocytes, leukemia cells, tumor cells or gliacells;
- promoter sequences of viruses such as HBV, HSV, HPV, EBV, HTLV, CMV or HIV;
- promoter or enhancer sequences which are activated by hypoxia;
- cell cycle-specific activation sequences of the genes encoding cdc25C, cyclin A, cdc2, E2F-1, B-myb and DHFR; and/or
- binding sequences, such as monomers or multimers of the Myc E box, for transcription factors which appear or are activated in a cell proliferation-dependent manner.

Various techniques can be used for combining the novel promoter with at least one further promoter. These techniques are described, for example, in DE19617851.7, DE19639103.2 and DE19651443.6.

In yet another preferred embodiment of the invention, a nucleic acid construct for the combination of the novel promoter with at least one further promoter or enhancer is selected. This construct contain the novel promoter in a form in which at least one binding site for a transcription factor is mutated. This mutation blocks initiation of transcription of the structural gene. Other components of the nucleic acid construct optionally are a structural gene, and at least one further promoter sequence or enhancer sequence which can be activated in either a nonspecific, cell-specific or virus-specific manner by tetracycline, and/or in a cell cycle-specific manner. The additional promoter may activate the transcription of at least one further structural gene which encodes at least one transcription factor, where the transcription factor is mutated so that it binds to the mutated binding site(s) of the novel promoter and activates this promoter, and/or the structural gene which encodes a transcription factor.

Figure 1:
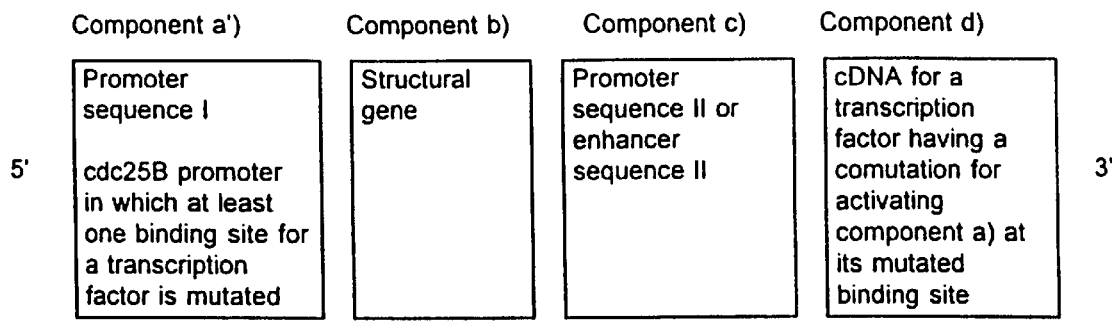
FIG. 1: Diagrammatic depiction of a novel nucleic acid construct comprising components (a)–(d).

Arrangement of the individual components is depicted, by way of example, by the diagram in FIG. 1.

In an exemplary embodiment of this invention, the mutation can be a mutation of the TATA box of the novel promoter. The TATA box (TATAAA or TATATAA) is recognized as a binding site for the initiation complex of the RNA polymerases II and III which are present in the cell nucleus. Initiation of transcription is effected some 30 bases downstream of the TATA box by binding the TATA box-binding protein (TBP), which is involved in the transcription reaction of all RNA polymerases (I, II and III) present in the cell nucleus. An example of a strictly TATA box-dependent promoter is the promoter for the U6 gene, which is transcribed by RNA polymerase III and whose gene product is involved in mRNA splicing.

An example of a mutation of the TATA box sequence can be TGTATAA. As a result of this mutation, the DNA-binding site of normal TBP no longer is recognized and the coding gene is no longer transcribed efficiently. In the case of such a mutation, the gene encoding the transcription factor is a nucleic acid sequence which encodes a comutated TBP. As a result of this comutation, the TBP binds to the mutated TATA box (e.g. to TGTATAA) and thereby leads to efficient transcription of the structural gene. Such comutations of the TBP gene have been described, for example, by Strubin and Struhl (*Cell*, 68:721 (1992)) and by Heard et al. (*EMBO J.*, 12:3519 (1993)).

A particularly preferred embodiment is a nucleic acid construct comprising:

(1) the novel promoter of the cdc25B gene, including the TATA box, with the sequence of the TATA box being mutated to TGTA, (2) the sequence GCCACC, (3) the cDNA for the immunoglobulin signal peptide (SEQ ID NO: 11) (nucleotide sequence $\leq 63$ to $>107$), (4) the cDNA for β-glucuronidase (SEQ ID NO: 12) (nucleotide sequence $\leq 93$ to $>1982$), (5) the promoter of the von Willebrand's Factor gene (SEQ ID NO: 13) (nucleotide sequence −487 to +247), and (6) the cDNA for the TATA box-binding protein (nucleic acid sequence from 1 to 1001, which is mutated at nucleic acid positions 862 (A replaced with T), 889 and 890 (GT replaced with AC) and 895 (C replaced with G)).

In another preferred embodiment the invention provides a nucleic acid construct comprising the novel promoter combined with at least one further promoter. The resulting combination is termed a multiple promoter. The multiple promoter contains a nuclear retention signal and an export factor, and comprises the following components:

(a) a first nonspecific, cell-specific or virus-specific promoter or enhancer sequence (I) which can be activated metabolically and/or cell cycle-specifically and which activates the basal transcription of a structural gene, (b) a structural gene, (c) a nuclear retention signal (NRS), whose cDNA is linked, directly or indirectly, at its 5' end, to the 3' end of the structural gene, with the transcription product of the nuclear retention signal preferably having a structure for binding a nuclear export factor, (d) a further promoter or enhancer sequence (II), which activates the basal transcription of a nuclear export factor (NEF), and (e) a nucleic acid which encodes a nuclear export factor (NEF) which binds to the transcription product of the nuclear retention signal and thereby mediates transport of the transcription product of the structural gene out of the cell nucleus.

At least one of the promoter components constitutes the novel promoter.

The first (I) promoter or enhancer sequence (a) and the second (II) promoter or enhancer sequence (d) may be identical or different and, optionally, may be activated nonspecifically, in cell-specific fashion, or virus-specifically. Activation may also be under metabolic control, for example by hypoxia. The promoter or enhancer sequence (a) and the promoter or enhancer sequence (d) also may constitute a further cell cycle-specific promoter. One possible arrangement of the individual components is shown in FIG. 2.

Figure 2:
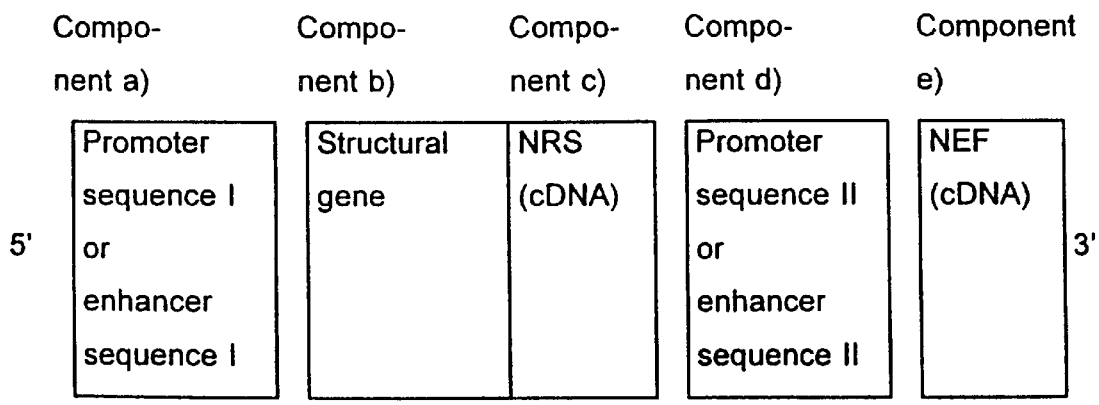
FIG. 2: Diagrammatic depiction of a novel nucleic acid construct comprising components (a)–(e).

In the novel nucleic acid constructs, components (d) and (e) can be located upstream (5') or downstream (3') of components (a),(b) and (c) (see FIG. 2). Preferably, the gene encoding the nuclear retention signal (NRS) is selected from the rev-responsive element (RRE) of HIV-1 or HIV-2, the RRE-equivalent retention signal of retroviruses or the RRE-equivalent retention signal of HBV.

The gene encoding the nuclear export factor (NEF) preferably is a gene selected from the rev gene of the HIV-1 or HIV-2 viruses, visna-maedi virus, caprine arthritis encephalitis virus, equine infectious anemia virus, feline immunodeficiency virus, retroviruses or HTLV, the gene encoding the hnRNP-A1 protein or the gene encoding the transcription factor TFIII-A.

In yet another preferred embodiment, at least one promoter or enhancer sequence (component (a) or (d)) in the novel nucleic acid constructs is a gene construct, termed an activator-responsive promoter unit, that preferably comprises the following components:

(f) one or more identical or different promoter or enhancer sequence(s) that may, for example, be activated in a cell cycle-specific manner, in cell proliferation-dependent fashion, by metabolic control, in cell- or virus-specific fashion, or the enhancer may be under both cell cycle-specific and metabolic, cell-specific or virus-specific control (so-called chimeric promoters), (g) one or more identical or different activator subunit(s) located downstream of the promoter or enhancer sequences and whose basal transcription is activated by those sequences, and h) an activator-responsive promoter which is activated by the expression products of one or more activator subunit(s).

Figure 3:
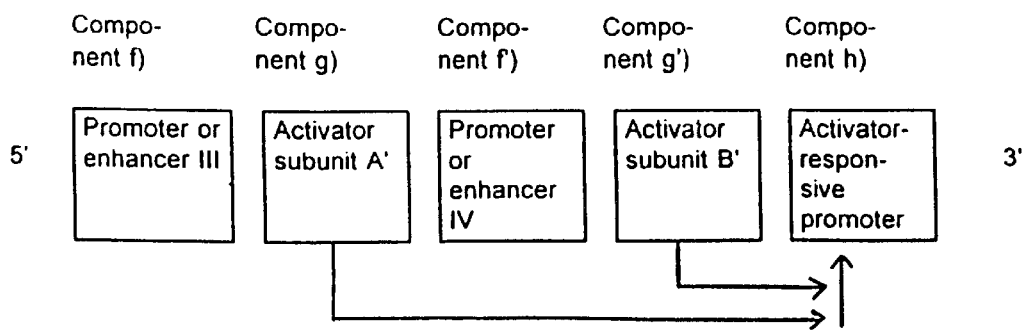
FIG. 3: Diagrammatic depiction of an activator-responsive promoter unit.

An arrangement of the individual components in a preferred activator-responsive promoter unit is illustrated in FIG. 3. Insertion of a preferred activator-responsive promoter unit into a novel nucleic acid construct is illustrated, for example, in FIG. 4.

Figure 4:
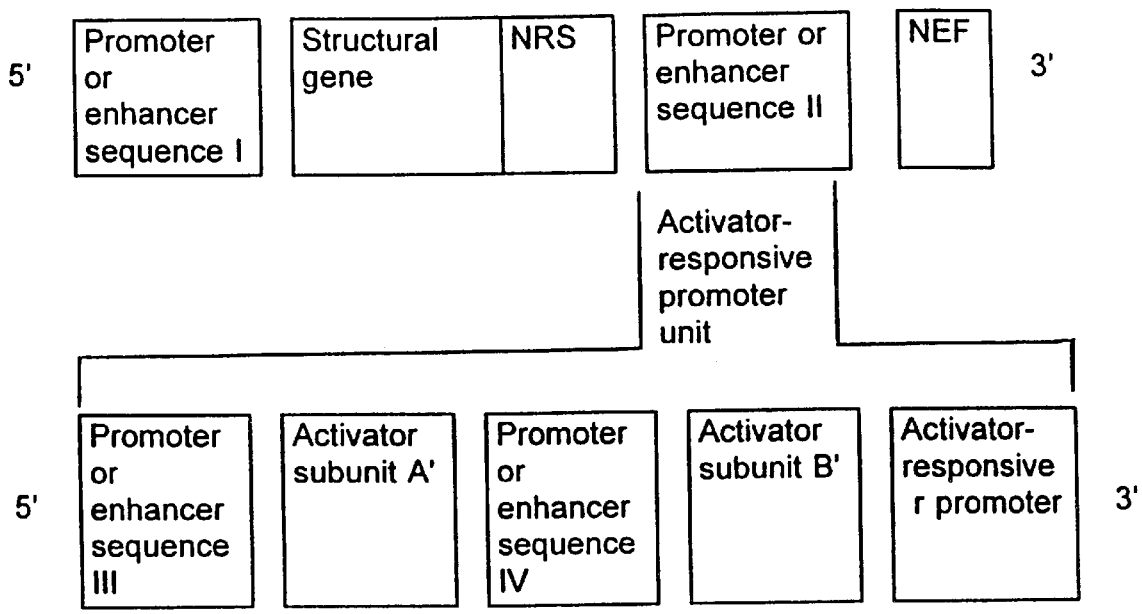
FIG. 4: Diagrammatic depiction of a novel nucleic acid construct comprising an activator-responsive promoter unit.

In the activator-responsive promoter units exemplified in FIGS. 3 and 4, at least one promoter (I, II, III or IV) can constitute the novel promoter. In a preferred embodiment, the activator-responsive promoter units may constitute binding sequences for chimeric transcription factors which are composed of DNA-binding domains, protein/protein interaction domains and transactivating domains. Each of the transcription factor-binding sites may be present once (monomers) or in several copies (multimers, for example, up to approximately 10 copies).

The LexA operator in combination with the SV40 promoter is an example of an activator-responsive promoter (h) which is activated by two activator subunits (g and g'). This promoter contains, for example, the following activator subunits:

(1) the first activator subunit (g) contains the cDNA encoding amino acids 1–81 or 1–202 of the LexA DNA-binding protein whose 3' end is linked to the 5' end of the cDNA encoding the Gal80 protein (amino acids 1–435), and (2) the second activator subunit (g') contains the cDNA encoding the Gal80-binding domain of the Gal4 protein (SEQ ID NO: 16) encoding amino acids 851–881, whose 3' end is linked to the 5' end of the cDNA encoding amino acids 126–132 of the SV40 large T antigen (SEQ ID NO: 9), whose 3' end in turn is linked to the 5' end of the cDNA encoding amino acids 406–488 of the transactivating domain of HSV-1 VP16 (SEQ ID NO: 14).

Another example of an activator-responsive promoter that is activated by two activator subunits (g and g') is the binding sequence for the Gal4 protein in combination with the SV40 promoter. This promoter contains, for example, the following activator subunits:

(1) the first activator subunit (g) contains the cDNA encoding the DNA-binding domain of the Gal4 protein (SEQ ID NO: 16) (amino acids 1–147), whose 3' end is linked to the 5' end of the cDNA for the Gal80 protein (amino acids 1–435), and (2) the second activator subunit (g') contains the cDNA encoding the Gal80-binding domain of Gal4 (SEQ ID NO: 16) (amino acids 851 to 881), whose 3' end is linked to the 5' end of the cDNA encoding the SV40 nuclear localization signal SV40 (SEQ ID NO: 9) (SV40 large T, amino acids 126–132), whose 3' end in turn is linked to the 5' end of the cDNA encoding amino acids 406–488 of the transactivating domain of HSV-1 VP16 (SEQ ID NO: 14).

Yet another example of two activator subunits (g and g') that activate the activator-responsive promoter containing the sequence for binding the Gal4 protein and the SV40 promoter is (1) the activating unit (g) which contains the cDNA encoding the cytoplasmic domain of the CD4 T cell antigen (amino acids 397–435), whose 5' end is linked to the 3' end of the cDNA for the transactivating domain of HSV-1 VP16 (SEQ ID NO: 14) (amino acids 406–488), whose 5' end in turn is linked to the 3' end of the cDNA for the SV40 nuclear localization signal (SV40 large T, amino acids 16–132), and (2) the activating unit (g') which contains the cDNA encoding the SV40 nuclear localization signal (SEQ ID NO: 9) (SV40 large T, amino acids 126–132) and the cDNA for the DNA-binding domain of the Gal4 protein (SEQ ID NO: 16) (amino acids 1–147), whose 3' end is linked to the 5' end of the cDNA for the CD4-binding sequence of the p56 lck protein (SEQ ID NO: 17) (amino acids 1–71).

A preferred embodiment is therefore a nucleic acid construct containing:

(1) one or more identical or different activator subunits whose basal transcription is activated by a promoter or enhancer, and (2) an activator-responsive promoter which is activated by the expression product of said activator subunit, A particularly preferred embodiment is a nucleic acid construct which contains, as an activator subunit (A), (1) the novel promoter, (2) the SV40 nuclear localization signal (SEQ ID NO: 9) (NLS) (SV40 large T, amino acids 126–132; PKKKRKV) (SEQ ID NO: 9), (3) the HSV-1 VP16 (SEQ ID NO: 14) acid transactivating domain (TAD) (amino acids 406 to 488), and (4) the cDNA encoding the cytoplasmic part of the CD4 glycoprotein (SEQ ID NO: 15) (amino acids 397–435);

and, as another activator subunit (B), (1) the promoter of the cdc25C gene (SEQ ID NO: 19) (nucleic acids −290 to +121), (2) the SV40 nuclear localization signal (SEQ ID NO: 9) (NLS) (SV40 large T; amino acids 126–132 PKKKRKV) (SEQ ID NO: 9), (3) the cDNA for the DNA-binding domain of the Gal4 protein (SEQ ID NO: 16) (amino acids 1 to 147), and (4) the cDNA for the CD4-binding sequence of the p56 lck protein (amino acids 1–71)

and also the activator-responsive promoter, containing up to about 10 copies of the binding sequence for the Gal4 binding protein, having the nucleotide sequence (SEQ ID NO: 8) 5'-CGGACAATGTTGACCG-3', and the basal SV40 promoter (SEQ ID NO: 18) (nucleotide sequence 48 to 5191);

and, where appropriate, a structural gene, preferably a complete cDNA encoding an active compound, an enzyme, or a fusion protein which is composed of a ligand and an active compound or a ligand and an enzyme.

As a rule, the structural gene is a gene encoding a pharmacologically active compound, preferably selected from the group consisting of enzymes, fusion proteins, cytokines, chemokines, growth factors, receptors for cytokines, receptors for chemokines, receptors for growth factors, peptides or proteins having an antiproliferative or cytostatic or apoptotic effect, antibodies or antibody fragments, angiogenesis inhibitors, peptide hormones, coagulation factors, coagulation inhibitors, fibrinolytic peptides or proteins, peptides or proteins having an effect on blood circulation, blood plasma proteins, antigens of infectious agents, such as bacterial antigens and parasitic antigens, antigens of cells or antigens of tumors, with the antigen bringing about an immune reaction, thrombosis-inducing substances, complement-activating proteins, virus coat proteins and/or ribozymes.

In the case of a ribozyme, the structural gene is preferably a gene that encodes a ribozyme which inactivates an mRNA encoding a protein selected from the group consisting of cell cycle control proteins, in particular cyclin A, cyclin B, cyclin D1, cyclin E, E2F1-5, cdc2, cdc25C or DP1, virus proteins, cytokines, growth factors and growth factor receptors.

In another preferred embodiment, the structural gene can be a gene encoding an enzyme that cleaves a drug precursor (a prodrug) into a drug.

In still another preferred embodiment, the structural gene can encode a ligand/effector fusion protein, where the ligand can be, for example, an antibody, an antibody fragment, a cytokine, a growth factor, an adhesion molecule or a peptide hormone, and the effector can be a pharmacologically active compound as described above or an enzyme. For example, the structural gene can encode a ligand/enzyme fusion protein, where the enzyme cleaves a precursor of a drug into a drug and the ligand binds to a cell surface, preferably to endothelial cells or tumor cells.

The nucleic acid constructs preferably are composed of DNA. The term nucleic acid constructs generally will be understood to include artificial structures composed of nucleic acids which can be transcribed in the target cells. Nucleic acid constructs preferably They are inserted into a vector, with plasmid vectors or viral vectors being particularly preferred.

In general, these vectors are administered to patients externally or internally, locally, perorally, intravesically, nasally, intrabronchially, intramuscularly, subcutaneously into a body cavity, into an organ, into the blood circulation, into the respiratory tract, into the gastrointestinal tract and/or into the urogenital tract and are used for the prophylaxis or therapy of a disease.

Using the novel nucleic acid constructs, a structural gene can be expressed cell-specifically, virus-specifically, under designated metabolic conditions and/or cell cycle-specifically, with the structural gene preferably being a gene which encodes either a pharmacologically active compound or an enzyme which cleaves an inactive precursor of a drug into an active drug. The structural gene can be selected so that the pharmacologically active compound or the enzyme is expressed together with a ligand as a fusion protein, where the ligand binds to the surface of cells, e.g. proliferating endothelial cells or tumor cells.

The present invention furthermore relates to a process for preparing a novel nucleic acid construct in which the individual components of the nucleic acid construct are connected to each other. The connecting of the individual components can be effected using generally known methods, for example, enzymatically using ligases.

The present invention additionally also relates to cells, in particular yeast or mammalian cells, which harbor a novel nucleic acid construct. In a particularly preferred embodiment, the nucleic acid constructs are introduced by transfection into host cell lines which then can be used for expressing the transgene. These cells consequently can be used for providing a drug for patients. A preferred use of the novel nucleic acid construct comprises treatment or prophylaxis of a disease, by introducing a nucleic acid construct into a target cell and expressing the construct in a manner that is nonspecific, virus-specific, target cell-specific, metabolically specific, or cell cycle-specific manner.

In one method of administering the constructs in vivo, endothelial cells can, for example, be isolated from blood and transfected in vitro with the novel nucleic acid construct. The transfected cells are then reinjected into the patient, for example, intravenously.

Cells that have been transfected in vitro also may be administered to patients in combination with a novel vector. This combination has the advantage that cells and vectors can in each case be administered or injected simultaneously or at different times, and at the same or different sites.

The present invention further provides, therefore, methods of using a novel nucleic acid construct or of a novel cell for preparing a drug for the treatment of a disease selected from the group consisting of tumor diseases, leukemias, autoimmune diseases, allergies, arthritides, inflammations, organ rejections, graft versus host reactions, blood coagulation diseases, circulatory diseases, anemia, infections, hormonal diseases and CNS damage. Particular preference is given to using an endothelial cell for preparing a novel drug.

The novel nucleic acid constructs do not occur in this form in nature, i.e. the structural gene is not naturally combined with the novel promoter.

In each case the choice of the promoters and the structural gene is determined by the particular application of the present invention. For example, WO96/06940, WO96/06938, WO96/06941, WO96/06939, DE19605274.2, DE19617851.7, DE19639103.2 and DE19651443.6 disclose a detailed description of the individual components, which also are described below.

I) Promoter sequences

Within the meaning of the present invention, promoter sequences include nucleotide sequences which, after binding transcription factors, activate the transcription of a structural gene downstream of the 3' end of the promoter sequences [components (a), (c), (f) or (f')]. The choice of the promoter sequence(s) to be combined with the cdc25B promoter depends on the disease to be treated and on the target cell to be transduced. Thus, it is possible for the additional promoter sequence to be activatable in an unrestricted manner, in a target cell-specific manner, under defined metabolic conditions, in a cell cycle-specific manner or in a virus-specific manner. Furthermore, identical or different promoter sequences may be employed in components (a),(c), (f) and/or (f'). Examples of the promoter sequences to be selected are: promoter and activator sequences which can be activated in an unrestricted manner, such as the promoter of RNA polymerase III, the promoter of RNA polymerase II, the CMV promoter and CMV enhancer, or the SV40 promoter; viral promoter sequences and activator sequences, such as those of HBV, HCV, HSV, HPV, EBV, HTLV or HIV. When the HIV promoter is used, preference is given to using the entire LTR sequence including the TAR sequence [position −453 to −80, Rosen et al., *Cell* 41:813 (1985)] as a virus-specific promoter.

The promoter sequences furthermore include metabolically activatable promoter and enhancer sequences such as the hypoxia-inducible enhancer (Semenza et al., *Proc. Nat'l Acad. Sci* 88:5680 (1991); McBurney et al., *Nucl. Acids Res.* 19:5755 (1991)); cell cycle-specifically activatable promoters, such as the promoters of the cdc25C gene, the cyclin A gene, the cdc2 gene, the B-myb gene, the DHFR gene or the E2F-1 gene, or binding sequences for transcription factors which appear or are activated during cell proliferation, such as binding sequences for c-myc proteins, where these binding sequences may include monomers or multimers of the nucleotide sequence which is designated the Myc E box (SEQ ID NO: 10) [5'-GGAAGCAGACCACGTGGTCTGCTTCC-3'; Blackwood et al., Science 251:1211, (1991)]; tetracyclin-activatable promoters, such as the tetracylin operator in combination with an appropriate repressor; chimeric promoters which constitute a combination of an upstream activator sequence which can be activated cell-specifically, metabolically or virus-specifically with a downstream promoter module which contains, for example, the CDE-CHR or E2FBS-CHR nucleotide sequence to which suppressor proteins bind and are thereby able to inhibit activation of the upstream activator sequence in the $G_0$ phase and $G_1$ phase of the cell cycle (WO96/06943; Lucibello et al., *EMBO J.* 14:12 (1994)); cell-specifically activatable promoters, such as promoters or activator sequences from promoters or enhancers of those genes which encode proteins which are preferentially formed in the selected cells.

Examples of cell-specifically activatable promoters are promoter and activator sequences which are activated in endothelial cells, such as the promoter and activator sequences of the genes which encode brain-specific endothelial glucose-1 transporter, endoglin, VEGF receptor 1 (flt-1), VEGF receptor 2 (flk-1 or KDR), til-1 or til-2, B61 receptor (Eck receptor), B61, endothelin, especially endothelin B or endothelin 1, endothelin receptors, in particular the endothelin B receptor, mannose 6-phosphate receptors, von Willebrand factor, IL-1α, IL-1β, IL-1 receptor, vascular cell adhesion molecule (VCAM-1), or synthetic activator sequences which comprise oligomerized sites for binding transcription factors which are preferentially or selectively active, for example in endothelial cells. An example is the transcription factor GATA 2, whose binding site in the endothelin 1 gene is 5'-TTATCT-3' [Lee et al., *J. Biol. Chem.* 266: 16188 (1991), Dormann et al., *J. Biol. Chem.* 267:1279 (1992) and Wilson et al., *Mol. Cell Biol.* 10:4854 (1990)]. Further cell-specifically activatable promoters are promoters or activator sequences which are activated in cells in the vicinity of activated endothelial cells, such as the promoter and activator sequences of the genes encoding VEGF, with the gene-regulatory sequences for the VEGF gene being the 5'-flanking region, the 3'-flanking region, the c-Src gene or the v-Src gene, or steroid hormone receptors and their promoter elements (Truss et al., *Endocr. Rev.* 14:459 (1993)), in particular the mouse mammary tumor virus promoter.

Examples of promoters or activator sequences which are activated in muscle cells, in particular in smooth muscle cells, are promoter and activator sequences of the genes which encode tropomyosin, α-actin, α-myosin, PDGF receptor, FGF receptor, MRF-4, phosphofructokinase A, phosphoglycerate mutase, troponin C, myogenin, endothelin A receptors, desmin, VEGF, where the gene-regulatory sequences for the VEGF gene are as described above, or "artificial" promoters. Examples of artificial promoters are multiple copies of the (DNA) binding site for muscle-specific helix-loop-helix (HLH) proteins such as the E box (Myo D) (e.g. 4x AGCAGGTGTTGGGAGGC, SEQ ID NO.: 1) or multiple copies of the DNA zinc finger protein GATA 4-binding site of the α-myosin heavy chain gene (e.g. 5'-GGCCGATGGGCAGATAGAGGGGGCCGATGGGCA GATAGAGG3', SEQ ID NO.: 2). Examples of HLH proteins are MyoD, Myf-5, myogenen, or MRF4. The HLH proteins, and also GATA 4, exhibit muscle-specific transcription not only with promoters of muscle-specific genes but also in a heterologous context, that is, with artificial promoters as well.

Promoter and activator sequences which are activated in glial cells are, in particular, the gene-regulatory sequences or elements from genes which encode, for example, the following proteins: the Schwann cell-specific protein periaxin, glutamine synthetase, the glial cell-specific protein (glial fibrillary acid protein=GFAP), the gliacell protein Sloob, IL-6, CNTF, 5-HT receptors, TNFα, IL-10, insulin-like growth factor receptor I and II or VEGF, where the gene-regulatory sequences for the VEGF gene are as described above.

Promoters and activator sequences which are activated in hematopoietic cells are promoter sequences for genes for cytokines or cytokine receptors which are expressed in hematopoietic cells or in adjacent cells, such as the stroma.

These promoter sequences include, for example, promoter sequences for the following cytokines and their receptors: stem cell factor receptor, stem cell factor, IL-1α, IL-1 receptor, IL-3, IL-3 receptor (α subunit), IL-3 receptor (α subunit), IL-6, IL-6 receptor, GM-CSF, GM-CSF receptor (α chain), interferon regulatory factor 1 (IRF-1), with the IRF-1 promoter being activated to an equal extent by IL-6 and by IFNγ or IFNβ, erythropoietin or erythropoietin receptor.

Examples of promoters and activator sequences which are activated in lymphocytes and/or macrophages are the promoter and activator sequences of genes for cytokines, cytokine receptors and adhesion molecules and receptors for the Fc fragment of antibodies.

Examples are the promoter sequences for the following proteins: IL-1 receptor, IL-1α, IL-1β, IL-2, IL-2 receptor, IL-3, IL-3 receptor (α subunit), IL-3 receptor (β subunit), IL-4, IL-4 receptor, IL-5, IL-6, IL-6 receptor, interferon regulatory factor 1 (IRF-1), with the IRF-1 promoter being activated to an equal extent by IL-6 as by IFNγ or IFNβ, IFNγ responsive promotor, IL-7, IL-8, IL-10, IL-11, IFNγ, GM-CSF, GM-CSF receptor (α chain), IL-13, LIF, macrophage colony-stimulating factor (M-CSF) receptor, Type I and Type II macrophage scavenger receptors, MAC-1 (leukocyte function antigen), LFA-1α (leukocyte function antigen) or p150,95 (leukocyte function antigen).

Promoter and activator sequences which are activated in synovial cells are, for example, the promoter sequences for matrix metalloproteinases (MMP), for example for MMP1 (interstitial collagenase) or MMP3 (stromelysin/transin). These sequences further include the promoter sequences for tissue inhibitors of metalloproteinases (TIMP), for example TIMP-1, TIMP-2 or TIMP-3.

Examples of promoters and activator sequences which are activated in leukemia cells are promoters for c-myc, HSP70, bcl-1/cyclin D1, bcl-2, IL-6, IL-10, TNFβ, TNFα, HOX11, BCR-Abl, E2A-PBX1, PML-RARA (promyelocytic leukemia retinoic acid receptor) or c-myc, with c-myc proteins binding to multimers of the nucleotide sequence termed an Myc E box (5'-GGAAGCAGACCAGCTGGTCTGCTTCC-3', SEQ ID NO.: 3) and activating them.

An example of promoters or activator sequences which are activated in tumor cells is a gene-regulatory nucleotide sequence which interacts with transcription factors which are formed or are active in tumor cells.

Preferred promoters or activator sequences include gene-regulatory sequences or elements from genes which encode proteins that are formed in cancer cells or sarcoma cells. Thus, the N-CAM promoter is preferred in the case of small-cell bronchial carcinomas, the promoter of the hepatitis growth factor receptor or of L-plastin is preferred in the case of ovarian carcinomas, and the promoter of L-plastin or of polymorphic epithelial mucin (PEM) is preferred in the case of pancreatic carcinomas.

II) Nuclear export signals and nuclear export factors

In a preferred embodiment, the nuclear retention signal (NRS) is a nucleotide sequence which, when linked to a premessenger RNA, impedes transport through the nuclear membrane, but which also constitutes a structure for binding an export protein. This export protein mediates the transport of an NRS-containing premessenger or messenger RNA out of the cell nucleus into the cytoplasm. A premessenger or messenger RNA which contains the NRS is consequently secreted out of the cell nucleus by being bound to the export protein (Fischer et al., *Cell*, 82:475 (1995)).

The nuclear export signals (NES) are preferably the retroviral rev-responsive element (RRE) sequence. In the case of HIV-1, this RRE is a sequence in the env gene encompassing 243 nucleotides (nucleotides 7362–7595). However, the nuclear export signal (NES) also can be any homologous and/or functionally similar (analogous) nucleotide sequence such as the RRE-equivalent element of the HBV virus (Huang et al., *Mol. Cell Biol.*, 13:7476 (1993)).

In the novel nucleic acid constructs, the nuclear export factor (NEF) is a nucleotide sequence which encodes a protein that binds to the ruRNA of the NRS and mediates the transport of the NRS-containing premessenger RNA or messenger RNA out of the cell nucleus and into the cytoplasm (or out of the cytoplasm and into the cell nucleus). The rev gene from retroviruses, especially from HIV-1 or HIV-2 virus, is used in particular. The rev protein from the retroviral rev gene binds via its N-terminal domain to the RRE in the pre-mRNA. The binding between the RRE and the rev protein enables nonspliced premessenger RNA, and also any other RNA which contains an RRE, to be transported out of the cell nucleus and into the cytoplasm, and thereby substantially augments translation.

Within the meaning of the present invention, nucleotide sequences which encode proteins that are homologous and functionally similar to the HIV-1 rev protein (Bogerd et al., *Cell*, 82:485 (1995)), such as the visna-maedi virus (VMV) rev gene or the caprine arthritis encephalitis virus (CAEV) rev gene, also can be used as NEFs. However, genes also can be employed that encode proteins which, while only possessing slight or no homology with the rev protein, nevertheless are functionally similar to the HIV-1 rev protein. Examples are the HTLV-1 rev gene and the equine infectious anemia virus (EIAV) and feline immunodeficiency virus (FIV) rev genes.

In an alternative embodiment, the NEFs also can be nucleotide sequences that encode proteins which allow secretion of RNA out of the nucleus without this RNA being retained in the nucleus by an NRS. Examples of such proteins are transcription factor TFIIIA or heterogeneous nuclear ribonuclear protein A1 (hnRNPA1 protein). In a wider sense, the nuclear transport proteins also include heat shock protein 70 (hsc70) and the protein kinase inhibitor CPKI.

Common features shared by the NEF and its homologous and analogous proteins are a domain, situated towards the amino terminus, for binding the monomeric NEF protein to the RNA of the NRS, and also a domain which is usually leucine-rich (hnRNPA1 is an exception to this), which is required for the transport function of the NEF.

Within the meaning of this invention, expression of the NEF gene is under the control of a promoter sequence which is located upstream at the 5' end of the NEF gene, as described above.

III) Structural genes

Within the meaning of the invention, the structural genes [component(b)] encode an active compound for the prophylaxis and/or therapy of a disease. Structural genes and promoter sequences may be selected with regard to the nature of the therapy of the disease, taking into consideration the target cell to be transduced.

For example, the combinations of promoter sequences and structural genes set forth below may be selected in association with the following diseases. Detailed descriptions are provided in Patent Applications WO96/06940, DE19605274.2, DE19617851.7, DE19639103.2 and DE19651443.6, the contents of which are hereby incorporated by reference in their entirety.

Examples of target cells which are selected for the therapy of tumors are: proliferating endothelial cells, stroma cells and muscle cells which adjoin the endothelial cell, tumor cells or leukemia cells. The promoters are endothelial cell-specific and cell cycle-specific or cell-nonspecific or muscle cell-specific and cell cycle-specific or tumor cell-specific (solid tumors and leukemias) and cell cycle-specific.

When selecting structural genes for inhibitors of cell proliferation, for example for retinoblastoma protein (pRb= p110) or the related p107 and p130 proteins, the following strategy may be used:

The retinoblastoma protein (pRb/p110) and the related p107 and p130 proteins are inactivated by phosphorylation. Preference is given to using those genes of these cell cycle inhibitors which exhibit mutations for the inactivation sites of the expressed proteins without concomitant impairment of function. Examples of these mutations have been described for p110. The DNA sequence for the p107 protein or the p130 protein can be mutated in an analogous manner.

The p53 protein is another inhibitor of cell proliferation. Protein p53 is inactivated in the cell either by binding to special proteins, such as MDM2, or by oligomerization of the p53 by way of the dephosphorylated C-terminal serine. Consequently, preferred genes include those encoding a truncated p53 that lacks serine 392 at the C terminus. Other inhibitors are p21 (WAF-1), the p16 protein, other cdk inhibitors, the GADD45 protein or the bak protein.

Structural genes for coagulation-inducing factors and angiogenesis inhibitors encode, for example, plasminogen activator inhibitor 1 (PAI-1), PAI-2, PAI-3, angiostatin, interferons (IFNα, IFNβ or IFNγ), platelet factor 4, IL-12, TIMP-1, TIMP-2, TIMP-3, leukemia inhibitory factor (LIF) or tissue factor (TF) and its fragments which are active in coagulation.

Structural genes for cytostatic and cytotoxic proteins encode, for example, perforin, granzyme, IL-2, IL-4, IL-12, interferons, such as IFNα, IFNβ or IFNγ, TNF, such as TNFα or TNFβ, oncostatin M, sphingomyelinase or magainin and magainin derivatives.

Structural genes which encode cytostatic or cytotoxic antibodies and fusion proteins between antigen-binding antibody fragments and cytostatic, cytotoxic or inflammatory proteins or enzymes can be chosen using the following strategy:

The cytostatic or cytotoxic antibodies include, for example, those which are directed against membrane structures of endothelial cells, as described, for example, by Burrows et al. (*Pharmac. Ther.*, 64:155 (1994)), Hughes et al., (*Cancer Res.*, 49:6214 (1989)) and Maruyama et al., (*Proc. Nat'l. Acad. Sci. USA*, 87:5744 (1990)). Such antibodies include, in particular, antibodies against the VEGF receptors. Other antibodies include cytostatic or cytotoxic antibodies which are directed against membrane structures on tumor cells. These antibodies have been reviewed, for example, by Sedlacek et al., *Contrib. to Oncol.*, 32, Karger Verlag, Munich (1988) and *Contrib. to Oncol.*, 43, Karger Verlag, Munich (1992). Other examples are antibodies against sialyl Lewis X or Y; against peptides on tumors that are recognized by T cells; against proteins which are expressed from oncogenes; against gangliosides such as GD3, GD2, GM2, 9-0-acetyl GD3 and fucosyl GM1; against blood group antigens and their precursors; against antigens on polymorphic epithelial mucin; and against antigens on heat shock proteins. Further examples include antibodies directed against membrane structures of leukemia cells. A large number of such monoclonal antibodies have already been described for diagnostic and therapeutic procedures (see reviews in Kristensen, *Danish Medical Bulletin*, 47:52 (1994); Schranz, *Therapia Hungarica*, 38:3 (1990); Drexler et al., *Leuk. Res.*, 10:279 (1986); Naeim, *Dis. Markers*, 71 (1989); Stickney et al., *Curr. Opin. Oncol.*, 4:847 (1992); Drexler et al., *Blut*, 57:327 (1988); Freedman et al., *Cancer Invest.*, 9:69 (1991)). Depending on the type of leukemia, monoclonal antibodies, or corresponding antigen-binding antibody fragments, which are directed against the following membrane antigens are, for example, suitable for use as ligands:

| Cells | Membrane antigen |
|---|---|
| AML | CD13 |
| | CD15 |
| | CD33 |
| | CAMAL |
| | sialosyl-Le |
| B-CLL | CD5 |
| | CD1c |
| | CD23 |
| | idiotypes and isotypes of the membrane immunoglobulins |
| T-CLL | CD33 |
| | M38 |
| | IL-2 receptors |
| | T cell receptors |
| ALL | CALLA |
| | CD19 |
| | non-Hodgkin's lymphoma |

Methods for humanizing murine antibodies, and for preparing and optimizing genes for Fab and recombinant Fv fragments are well known in the art (Winter et al., *Nature*, 349:293 (1991); Hoogenbooms et al., *Rev. Tr. Transfus. Hemobiol.*, 36:19 (1993); Girol. *Mol. Immunol.*, 28:1379 (1991) or Huston et al., *Intern. Rev. Immunol.*, 10:195 (1993)). Recombinant Fv fragments also may be fused with genes for cytostatic, cytotoxic or inflammatory proteins or enzymes using methods that are known in the art.

Structural genes which encode fusion proteins between target cell-binding ligands and cytostatic and cytotoxic proteins can be selected as set forth below. The ligands include, for example, all substances which bind to membrane structures or membrane receptors on endothelial cells. Examples of these substances are cytokines, such as IL-1, or growth factors, or their fragments or part sequences thereof, which bind to their corresponding receptors which are expressed by endothelial cells, for example PDGF, bFGF, VEGF, TGF.

Other ligands include adhesion molecules which bind to activated and/or proliferating endothelial cells. Examples of these are SLex, LFA-1, MAC-1, LECAM-1, VLA-4 or vitronectin. Substances which bind to membrane structures or membrane receptors of tumor or leukemia cells also are included. Examples are growth factors, or their fragments or part sequences thereof, which bind to their corresponding receptors which are expressed by leukemia cells or tumor cells. Such growth factors have already been described (reviews in Cross et al., Cell, 64:271 (1991), Aulitzky et al., *Drugs*, 48:667 (1994), Moore, *Clin. Cancer Res.*, 1:3 (1995), Van Kooten et al., *Leuk. Lymph.*, 27 (1993)). The genes for these ligands, which bind to the target cell, are fused with the genes for cytostatic, cytotoxic or inflammatory proteins or enzymes using methods that are well known in the art.

Structural genes for inflammation inducers may encode, for example, IL-1, IL-2, RANTES (MCP-2), monocyte chemotactic and activating factor (MCAF), IL-8, macrophage inflammatory protein 1 (MIP-1α, MIP-1β), neutrophil activating protein 2 (NAP-2), IL-3, IL-5, human leukemia inhibitory factor (LIF), IL-7, IL-11, IL-13, GM-CSF, G-CSF, M-CSF, cobra venom factor (CVF), or part sequences of CVF which correspond functionally to human complement factor C3b, i.e. which are able to bind to complement factor B and which, after cleavage by factor D, constitute a C3 convertase, human complement C3 or its part sequence C3b, cleavage products of human complement factor C3 which resemble CVF functionally and structurally, or bacterial proteins which activate a complement or induce inflammations, for example Salmonella typhimurium porins, Staphylococcus aureus clumping factors, modulins, particularly from Gram-negative bacteria, major outer membrane protein from Legionellas or from Haemophilus influenzae type B or from Klebsiellas, or M molecules from group G Streptococci.

Structural genes which encode enzymes for activating precursors of cytostatic agents, for example genes which encode enzymes that cleave inactive precursors (prodrugs) into active cyctostatic agents (drugs), and the relevant prodrugs and drugs in each case, are described by Deonarain et al. (*British Journal Cancer*, 70:786 (1994)), Mullen, *Pharmac. Ther.*, 63:199 (1994)) and Harris et al. (*Gene Ther.*, 1:170 (1994)). For example, the DNA sequence for one of the following enzymes can be used: herpes simplex virus thymidine kinase, varicella zoster virus thymidine kinase, bacterial nitroreductase, bacterial β-glucuronidase, plant β-glucuronidase from Secale cereale, human β-glucuronidase, human carboxypeptidase (CB) for example mast cell CB-A, CB-B, pancreatic or bacterial carboxypeptidase, bacterial β-lactamase, bacterial cytosine deaminase, human catalase or peroxidase, phosphatase, in particular human alkaline phosphatase, human acid prostate phosphatase or type 5 acid phosphatase, oxidase, in particular human lysyl oxidase or human acid D-aminooxidase, peroxidase, in particular human glutathione peroxidase, human eosinophilic peroxidase or human thyroid peroxidase, or galactosidase.

In addition, the therapy of autoimmune diseases and inflammations is described in WO/06941 and DE19651443.6, which are hereby incorporated by reference in their entirety.

Examples of suitable target cells are proliferating endothelial cells, macrophages and/or lymphocytes or synovial cells. The promoters may be, for example, endothelial cell-specific and cell cycle-specific or macrophage-specific and/or lymphocyte-specific and/or cell cycle-specific or synovial cell-specific and/or cell cycle-specific.

The structural genes for the therapy of allergies encode, for example, IFNβ, IFNγ, IL-10, antibodies or antibody fragments against IL-4, soluble IL-4 receptors, IL-12 or TGFβ.

The structural genes for preventing the rejection of transplanted organs encode, for example, IL-10, TGFβ, soluble IL-1 receptors, soluble IL-2 receptors, IL-1 receptor antagonists, soluble IL-6 receptors or immunosuppressive antibodies or their VH-containing and VL-containing fragments or their VH and VL fragments which are connected by way of a linker. Examples of immunosuppressive antibodies are antibodies which are specific for the T cell receptor or its CD3 complex, or are directed against CD4 or CD8, and, in addition, against the IL-2 receptor, IL-1 receptor or IL-4 receptor or against the adhesion molecules CD2, LFA-1, CD28 or CD40.

The structural genes for the therapy of antibody-mediated autoimmune diseases encode, for example, TGFβ, IFNα, IFNβ, IFNγ, IL-12, soluble IL-4 receptors, soluble IL-6 receptors or immunosuppressive antibodies or their VH-containing and VL-containing fragments.

The structural genes for therapy of cell-mediated autoimmune diseases encode, for example, IL-6, IL-9, IL-10, IL-13, TNFα or TNFβ, IL-13 or an immunosuppressive antibody or its VH-containing and VL-containing fragments.

The structural genes for inhibitors of cell proliferation, cytostatic or cytotoxic proteins and enzymes for activating precursors of cytostatic agents have already been listed above in relation to the therapy of tumors.

The present invention also contemplates use of structural genes which encode fusion proteins between antibodies or Fab or recombinant Fv fragments of these antibodies, or other target cell-specific ligands, and the aforementioned cytokines, growth factors, receptors, cytostatic or cytotoxic proteins and enzymes.

The invention also methods for the therapy of arthritis using structural genes whose expressed protein directly or indirectly inhibits inflammation, for example in a joint, and/or promotes the reconstitution of extracellular matrix (cartilage and connective tissue) in the joint.

Examples of such proteins are: IL-1 receptor antagonist (IL-1-RA), since IL-1-RA inhibits the binding of IL-1α and IL-1β; soluble IL-1 receptor, since soluble IL-1 receptor binds and inactivates IL-1; IL-6, since IL-6 increases the secretion of TIMP and superoxides and decreases the secretion of IL-1 and TNFα by synovial cells and chondrocytes; soluble TNF receptor, since soluble TNF receptor binds and inactivates TNF; IL-4, since IL-4 inhibits the formation and secretion of IL-1, TNFα and MMP; IL-10, since IL-10 inhibits the formation and secretion of IL-1, TNFα, and MMP and increases the secretion of TIMP; insulin-like growth factor (IGF-1), since IGF-1 stimulates the synthesis of extracellular matrix, TGFβ, especially TGFβ1 and TGFβ2, since TGFβ stimulates the synthesis of extracellular matrix; and superoxide dismutase or TIMP, especially TIMP-1, TIMP-2 or TIMP-3.

The therapy of the deficient formation of blood cells has already been described in detail in WO96/06941, which is hereby incorporated by reference in its entirety.

Examples of suitable target cells are proliferating, immature cells of the hematopoietic system or stroma cells which are adjacent to the hematopoietic cells. The promoters are, for example, specific for hematopoietic cells and/or are cell cycle-specific or cell-nonspecific and cell cycle-specific.

A structural gene for the therapy of anemia encodes erythropoietin, for example. Structural genes for the therapy of leukopenia encode, for example, G-CSF, GM-CSF or M-CSF. Structural genes for the therapy of thrombocytopenia encode, for example, IL-3, leukemia inhibitory factor (LIF), IL-11 or thrombopoietin.

Suitable target cells for the therapy of damage to the nervous system are: glia cells or proliferating endothelial cells. In this case, the promoters are glia cell-specific and cell cycle-specific or endothelial cell-specific and cell cycle-specific or nonspecific and cell cycle-specific.

The structural genes for neuronal growth factors encode, for example, FGF, nerve growth factor (NGF), brain-derived neurotrophic factor (BDNF), neurotrophin 3 (NT-3), neurotrophin 4 (NT-4), ciliary neurotrophic factor (CNTF), or glial cell derived growth factor (GDNF). The structural genes for enzymes encode, for example, tyrosine hydroxylase or dopa decarboxylase. The structural genes for cytokines and their inhibitors which inhibit or neutralize the neurotoxic effect of TNFα encode, for example: TGFβ; soluble TNF receptors, since TNF receptors neutralize TNFα; IL-10, since IL-10 inhibits the formation of IFNγ; TNFα, IL-2 and IL-4; soluble IL-1 receptors, IL-1 receptor I, and IL-1 receptor II, since soluble IL-1 receptors neutralize the activity of IL-1; IL-1 receptor antagonist or soluble IL-6 receptors.

The therapy of disturbances of the blood coagulation system and the blood circulatory system already has been described in detail in Patent Applications WO96/06938, DE19617851.7 and DE19639103.2, which are hereby incorporated by reference in their entirety. Examples of suitable target cells are endothelial cells, proliferating endothelial cells, somatic cells in the vicinity of endothelial cells and smooth muscle cells or macrophages.

The promoters are, for example, cell-nonspecific and cell cycle-specific or specific for endothelial cells, smooth muscle cells or macrophages and cell cycle-specific.

Structural genes for the inhibition of coagulation or for promoting fibrinolysis encode, for example, tissue plasminogen activator (tPA), urokinase-type plasminogen activator (uPA), hybrids of tPA and uPA, protein C, hirudin, serine proteinase inhibitors (serpins), such as C-1S inhibitor, α1-antitrypsin or antithrombin III or tissue factor pathway inhibitor (TFPI). Structural genes for promoting coagulation encode, for example, F VIII, F IX, von Willebrand factor, F XIII, PAI-1, PAI-2 or tissue factor and fragments thereof. Structural genes for angiogenesis factors encode, for example, VEGF or FGF. Structural genes for lowering the blood pressure encode, for example, kallikrein or endothelial cell nitric oxide synthase. Structural genes for inhibiting proliferation of smooth muscle cells following damage to the endothelial layer encode, for example, an antiproliferative, cytostatic or cytotoxic protein or an enzyme for cleaving precursors of cytostatic agents into cytostatic agents, as have already been cited above under tumor therapy, or a fusion protein of one of these active compounds with a ligand, for example an antibody or antibody fragments which is/are specific for muscle cells. Structural genes for other blood plasma proteins encode, for example, albumin, C1 inactivator, serum cholinesterase, transferrin or 1-antritrypsin.

The use of nucleic acid constructs for vaccinations has already been described in detail in Patent Applications WO96/06941, DE19617851.7, DE19639103.2 and DE19651443.6, which are hereby incorporated by reference in their entirety. Examples of suitable target cells are muscle cells, macrophages and/or lymphocytes or endothelial cells. The promoters are, for example, nonspecific and cell cycle-specific or target cell-specific and cell cycle-specific.

The DNA for a protein which is formed by an infectious agent and which leads, by inducing an immune reaction, i.e. by means of antibody binding and/or by means of cytotoxic T lymphocytes, to the neutralization and/or destruction of the agent, is used, for example, as a structural gene for the prophylaxis of infectious diseases. Such so-called neutralization antigens already are employed as vaccination antigens (see review in Ellis, *Adv. Exp. Med. Biol.*, 327;263 (1992)). However, the possibilities of preparing effective vaccines by conventional methods are limited. Furthermore, the efficacy of DNA vaccines has been questioned (Fynan et al., *Int. J. Immunopharm.*, 17:79 (1995); Donnelly et al., *Immunol.* 2:20 (1994)). An advantage of the present invention is that it is possible to count on the efficacy being greater.

The present invention therefore preferably contemplates use of a DNA which encodes neutralization antigens from the following pathogenic agents: influenza A virus, HIV, rabies virus, HSV (herpes simplex virus), RSV (respiratory syncytial virus), parainfluenza virus, rotavirus, VzV (varicella zoster virus), CMV (cytomegalovirus), measles virus, HPV (human papilloma virus), HBV (hepatitis B virus), HCV (hepatitis C virus), HDV (hepatitis D virus), HEV (hepatitis E virus), HAV (hepatitis A virus), *Vibrio cholera* antigen, *Borrelia burgdorferi* or *Helicobacter pylori* or malaria antigen.

Other active substances of this nature also include the DNA for an antiidiotype antibody, or its antigen-binding fragments, whose antigen-binding structures (the complementarity determining regions) constitute copies of the protein structure or carbohydrate structure of the neutralization antigen of the infectious agent. Antiidiotype antibodies can, in particular, replace carbohydrate antigens in the case of bacterial infectious agents. Antiidiotype antibodies and their cleavage products have been reviewed by Hawkins et al. (*J. Immunother.*, 14:273 (1993)) and Westerink et al. (*Springer Seminars in Immunopathol.*, 15:227 (1993)). Examples of structural genes for "tumor vaccines" are genes which encode antigens on tumor cells. These antigens have been reviewed, for example, by Sedlacek et al., *Contrib. to Oncol.*, 32, Karger Verlag, Munich (1988) and *Contrib. to Oncol.*, 43, Karger Verlag, Munich (1992).

Other examples are genes which encode the following antigens or the following antiidiotype antibodies: sialyl Lewis X or Y, peptides on tumors which are recognized by T cells, proteins which are expressed from oncogenes, blood group antigens and their precursors, antigens on polymorphic epithelial mucin or antigens on heat shock proteins.

The therapy of chronic infectious diseases has already been described in detail in Patent Applications WO96/06941, DE19617851.7, DE19639103.2 and DE19651443.6, which are hereby incorporated by reference in their entirety. A suitable target cell is a liver cell, a lymphocyte and/or macrophage, an epithelial cell or an endothelial cell. The promoters are, for example, virus-specific or cell-specific and cell cycle-specific.

Structural genes encode, for example, a protein which exhibits cytostatic, apoptotic or cytotoxic effects, or an enzyme which cleaves a precursor of an antiviral or such cytotoxic substance into the active substance. Examples of structural genes which encode antiviral proteins are the genes for cytokines and growth factors which have an antiviral effect, for example IFNα, IFNβ, IFNγ, TNFα, TNFβ, IL-1 or TGFβ, or antibodies having a specificity which inactivates the relevant virus, or their VH-containing and VL-containing fragments, or their VH and VL fragments which are joined by way of a linker, as described above. Examples of antibodies against virus antigen are: anti-HBV, anti-HCV, anti-HSV, anti-HPV, anti-HIV, anti-EBV, anti-HTLV, anti-Coxsackie virus or anti-Hanta virus. Another example of an antiviral protein is a rev-binding protein. This protein binds to the rev-RNA and inhibits rev-dependent posttranscriptional steps in retrovirus gene expression. Examples of rev-binding proteins are RBP9-27, RBP1-8U, RBP1-8D or pseudogenes of RBP1-8.

Another viral structural gene encodes ribozymes which digest the mRNA of genes for cell cycle control proteins or the mRNA of viruses. Ribozymes which are catalytic for HIV have been reviewed, for example, by Christoffersen et al., *J. Med. Chem.*, 38:2033 (1995).

Examples of structural genes which encode antibacterial proteins are genes for antibodies which neutralize bacterial toxins or opsonize bacteria. Examples of these antibodies are antibodies against C or *B Meningococci*, *E. coli*, Borrelia, Pseudomonas, *Helicobacter pylori* or *Staphylococcus aureus*.

IV) Combination of identical or different structural genes

Detailed description are provided in WO96/06941, WO96/06939, WO96/06940, WO96/06938, DE19639103.2 and DE19651443.6, which are incorporated herein by reference in their entirety. An example of a combination of structural genes is a self-enhancing expression system that, where appropriate, is pharmacologically controllable, wherein the DNA sequences of two identical or two different structural genes [component (c) and (c')] are combined. A further promoter sequence or, preferably, the cDNA for an internal ribosome entry site (IRES) is placed, as a regulatory element, between the two structural genes for the purpose of expressing the two DNA sequences. An IRES makes it possible to express two DNA sequences which are joined to each other by way of an IRES. Such IRESs have been described, for example, by Montford et al. (*Trends in Genetics* 11:179 (1995); Kaufman et al., *Nucl. Acids Res.*, 19:4485 (1991); Morgan et al., *Nucl. Acids Res.*, 20:1293 (1992); Dirks et al., *Gene*, 128:247 (1993); Pelletier et al., *Nature*, 334:320 (1988) and Sugitomo et al., *BioTechn.*, 12:694 (1994)). Thus, the cDNA for the polio virus IRES sequence (position <140 to >630 of the 5' UTR) can, for example, be used.

Preference is given to structural genes which exhibit an additive effect and which are linked by way of further promoter sequences or an IRES sequence. Preferred combinations of structural genes for the therapy of tumors encode, for example, identical or different, cytostatic, apoptotic, cytotoxic or inflammatory proteins and/or identical or different enzymes for cleaving the precursor of a cytostatic agent; preferred combinations for the therapy of autoimmune diseases encode different cytokines or receptors, having a synergistic effect, for inhibiting the cellular and/or humoral immune reaction, or different or identical TIMPs; preferred combinations for the therapy of the deficient formation of blood cells encode different, hierarchically consecutive cytokines such as IL-1, IL-3, IL-6 or GM-CSF and erythropoietin, G-CSF or thrombopoietin; preferred combinations for the therapy of nerve cell damage encode a neuronal growth factor and a cytokine or the inhibitor of a cytokine; preferred combinations for the therapy of disturbances of the blood coagulation system and blood circulatory system encode an antithrombotic agent and a fibrinolytic agent (e.g. tPA or uPA) or a cytostatic, apoptotic or cytotoxic protein and an antithrombotic agent or a fibrinolytic agent, or several different, synergistically acting blood coagulation factors, for example F VIII and vWF or F VIII and F IX; preferred combinations for vaccines encode an antigen and an immunostimulatory cytokine, for example IL-1α, IL-1β, IL-2, GM-CSF, IL-3 or IL-4 receptor, different antigens of one infectious agent or of different infectious agents, or different antigens of one tumor type or of different tumor types; preferred combinations for the therapy of viral infectious diseases encode an antiviral protein and a cytostatic, apoptotic or cytotoxic protein, or antibodies against different surface antigens of one virus or several viruses; and preferred combinations for the therapy of bacterial infectious diseases encode antibodies against different surface antigens and/or toxins of a causative organism.

V) Insertion of signal sequences and transmembrane domains

A detailed description has already been given in Patent Applications DE19639103.2 and DE19651443.6, which are incorporated herein by reference.

In order to enhance the translation, the nucleotide sequence GCCACC or GCCGCC (Kozak, *J. Cell Biol.*, 108:299 (1989)) can be inserted at the 3' end of the promoter sequence and directly at the 5' end of the start signal (ATG) of the signal or transmembrane sequence.

In order to facilitate secretion of the expression product of the structural gene, the homologous signal sequence which may be present in the DNA sequence of the structural gene can be replaced with a heterologous signal sequence which improves extracellular secretion. Thus, the signal sequence for immunoglobulin (DNA position 63 to 107; Riechmann et al., *Nature*, 332:323 (1988)) or the signal sequence for CEA (DNA position 33 to 134; Schrewe et al., *Mol. Cell Biol.*, 10:2738 (1990); Berling et al., *Cancer Res.*, 50:6534 (1990)) or the signal sequence of human respiratory syncytial virus glycoprotein (cDNA for amino acids 38 to 50 or 48 to 65; Lichtenstein et al., *J. Gen. Virol.*, 77:109 (1996)) can, for example, be inserted.

A sequence for a transmembrane domain can be inserted, as an alternative, or in addition, to the signal sequence in order to anchor the active compound in the cell membrane of the transduced cell which is forming the active compound. For example, the transmembrane sequence of human macrophage colony-stimulating factor (DNA position 1485 to 1554; Cosman et al., *Behring Inst. Mitt.*, 77:15 (1988)) or the DNA sequence for the signal and transmembrane regions of human respiratory syncytial virus (RSV) glycoprotein G (amino acids 1 to 63 or their part sequences, amino acids 38 to 63; Vijaya et al., *Mol. Cell Biol.*, 8:1709 (1988); Lichtenstein et al., *J. Gen. Virol.*, 77:109 (1996)) or the DNA sequence for the signal and transmembrane regions of influenza virus neuraminidase (amino acids 7 to 35 or the part sequence amino acids 7 to 27; Brown et al., *J. Virol.*, 62:3824 (1988)) can, for example, be inserted between the promoter sequence and the sequence of the structural gene. However, the nucleotide sequence for a glycophospholipid anchor also can be inserted in order to anchor the active compound in the cell membrane of the transduced cells which are forming the active compound. A glycophospholipid anchor is inserted at the 3' end of the nucleotide sequence for the structural gene. This insertion may be made in addition to inserting a signal sequence. Glycophospholipid anchors have been described, for example, for CEA, for N-CAM and for other membrane proteins, for example Thy-1 (see review in Ferguson et al., *Ann. Rev. Biochem.*, 57:285 (1988)).

Another option for anchoring active compounds to the cell membrane in accordance with the present invention is that of using a DNA sequence for a ligand/active compound fusion protein. The specificity of the ligand of this fusion protein is directed against a membrane structure on the cell membrane of the selected target cell.

The ligands which bind to the surface of cells include, for example, antibodies or antibody fragments which are directed against structures on the surface of endothelial cells, for example. These antibodies or antibody fragments include, in particular, antibodies against the VEGF receptors or against kinin receptors. They also can be directed against muscle cells, such as antibodies against actin or antibodies against angiotensin II receptors or antibodies against receptors for growth factors, such as against EGF receptors or against PDGF receptors or against FGF receptors, or antibodies against endothelin A receptors. The ligands also may include antibodies or their fragments which are directed against tumor-specific or tumor-associated antigens on the tumor cell membrane. Antibodies of this nature already have been described. Murine monoclonal antibodies preferably are employed in humanized form. Fab and recombinant Fv fragments, and their fusion products, are prepared using methods which are known to the skilled artisan, as described above.

The ligands furthermore include all active compounds, such as cytokines or adhesion molecules, growth factors or their fragments or part sequences thereof, mediators or peptide hormones which bind to membrane structures or membrane receptors on the relevant selected cell. Examples are ligands for endothelial cells, such as IL-1, PDGF, bFGF, VEGF, TGFβ (Pusztain et al., *J. Pathol.*, 169:191 (1993)) or kinin and derivatives or analogs of kinin. These ligands also include adhesion molecules. Adhesion molecules of this nature, such as SLex, LFA-1, MAC-1, LeCAM-1, VLA-4 or vitronectin and derivatives or analogs of vitronectin, already have been described for endothelial cells (see reviews in Augustin-Voss et al., *J. Cell Biol.*, 119:483 (1992); Pauli et al., *Cancer Metast. Rev.*, 9:175 (1990); Honn et al., *Cancer Metast. Rev.*, 11:353 (1992); Varner et al., *Cell Adh. Commun.*, 3:367 (1995)).

The present invention, thus generally described, will be understood more readily by reference to the following figures, tables and examples, which are provided by way of illustration and are not intended to be limiting of the present invention.

EXAMPLES

Example 1

Cloning and analysis of the murine cdc25B promoter

To clone the murine cdc25B promoter, approximately 106 phage plaques from a murine genomic phage library (mouse strain 129 FVJ, Stratagene) were screened in λ-Fix (Stratagene). The probe used in this screening was an 80 bp oligonucleotide directed against the region upstream of the 5' region of the murine cdc25B cDNA (Kakizuka et al., *Genes Dev.*, 6, 587 (1992)). The sequence is:

Probe 1:

(SEQ ID NO.: 4)

5'TCTAGCTAGCCTTTGCCCGCCCCGCCACGATGGA-

GGTACCCCTGCAGAAGTCTGCGCCGGGTTCAGCTCTCAGTCCTGCC-3'.

Three of the resulting six phage clones were isolated, amplified and mapped by means of restriction digestion (enzymes from Gibco) using two additional probes directed against other 3'-located sequences of the murine cdc25B cDNA (FIG. 5).

Probe 2:

(SEQ ID NO.: 5)

5'GGTCATTCAAAATGAGCAGTTACCATAAAACGCTTCCGATCCTTACCAG

TGAGGCTTCGTGGAACACAGTCCGGTGCTG-3'

Probe 3:

(SEQ ID NO.: 6)

5'GTTAAAGAAGCATTGTTATTATGGGAGGGGGGAGCAACCTCTGGGTTC

AGAATCTACATATGCTGGAAGGCCCCAATGA-3'

Finally, a 4.6 kb fragment from the proximal enhancer region, bordering on the published cDNA (Kakizuka et al., see above), was excised from phage VI using the enzymes EcoRI and SalI (Gibco) purified by agarose gel electrophoresis and using QIAquick™ spin columns (Qiagen), and inserted into a Bluescript SKII vector (Stratagene) (FIG. 5). 1.5 kb of the 3' region of the cloned 4.6 kb was sequenced and identified, by comparing the sequence with cdc25B cDNA sequences from various species, as being the murine homolog of the cdc25B gene.

Various fragments were excised from this sequenced region, cloned into a pGL3 luciferase reporter vector (Promega) and tested for promoter activity in NIH-3T3 mouse fibroblasts (ATCC). The (transient) transfection was carried out using the DEAE/dextran method (modified after Sompayrac et al., *Proc. Nat'l Acad. Sci. USA*, 78:7575 (1981)). The controls used in these experiments were the SV40 basal promoter in the pGL3 vector (Promega), which is not subject to any significant cell cycle regulation, and, as a positive control, a fragment of the human cdc25C promoter (SEQ ID NO: 19) (C290, Lucibello et al., *EMBO J.*, 14:132 (1995)), which also was cloned into the pGL3 vector. The luciferase activity was determined as described in Herber et al., *Oncogene*, 9, 1295 (1994).

The nucleotide sequence −950 to +167 was found to be the promoter of the murine c25B gene (SEQ ID NO.: 7, see Tab. 1).

Various deletion fragments were excised from the promoter of the murine cdc25B gene (FIG. 6), cloned into a pGL3 luciferase reporter vector (Promega), and tested for promoter activity, as described above, in NIH-3T3 mouse fibroblasts.

In order to analyze the cell cycle reaction of the different deletion constructs, normally growing, transiently transfected cells were compared with similar cells which were deprived of serum after transfection, as described (Lucibello et al., *EMBO J.*, 14:132 (1995)). The results are summarized in Table 2. The longest construct, i.e. B-950 (nucleotide sequence −950 to +167) (SEQ ID NO: 7), exhibited a cell cycle regulation of 10.1, which was comparable with that of the human cdc25C construct (not shown in Table 2). Deletion of the 3' region down to +3 (see FIG. 6) did not result in any loss of activity or cell cycle regulation of the promoter. It was possible, therefore, to delimit the region responsible for promoter regulation still further. The deletions of the 5' region of the promoter gave rise to two different effects; on the one hand, deletion of the longest construct, i.e. B-950, down to B-340 resulted in an increase in activity in $G_0/G_1$ cells, corresponding to a deregulation. Further deletions brought about a lowering of promoter activity until the last deletion, which brought about renewed deregulation (Table 2a).

The start site was determined by primer extension. For this, RNA was isolated from normally growing NIH-3T3 mouse fibroblasts and the reaction was carried out using different primers and MMLV reverse transcriptase (Gibco). The mapped start site is located in an initiator-like sequence element, 24 base pairs 3' of the TATA box (SEQ ID NO.: 7, see Tab. 3).

When the promoter activity of the deletion constructs is viewed against the background of the putative transcription factor-binding sites listed in Table 3, it is evident that these effects are mediated by the deletion of specific binding sites: deletion of the E boxes situated in the 5' region, like deletion of the putative E2F-binding site situated in the vicinity of the TATA box, leads to derepression of the promoter. Conversely, the deletions of the putative activator-binding sites (predominantly Sp1-binding sites) and an NF-Y-binding site diminish promoter activity (see Table 2b). In this context, the point mutation of the putative NF-Y site resulted in an activity loss of more than 74% as compared with the wild-type construct (see Table 2b). Electrophoretic mobility shift assays (EMSAs, as described in Zwicker et al., *Nucleic Acids Res.* 23, No. 19, S. 3822 ff., 1995) using specific antibodies against Sp1/Sp3 and NF-Y (Santa Cruz), and cross competition experiments with bona fide Sp1- or NF-Y-binding sites demonstrated specific binding of Sp1/Sp3 and NF-Y to the respective putative binding sites.

While the shortest construct (B-30), which contains the TATA box and the mapped start site, is to a large extent deregulated, it does exhibit an activity which is two hundred fold greater than the background activity of the pGL3 vector. Furthermore, point mutation of the TATA box resulted in a loss of more than 25% of the promoter activity (see Table 2a), thereby confirming its functional role in regulating promoter activity.

The transcription factor-binding sites (chiefly SP1 and NF-Y) correspond to those of many described genes which are regulated in a cell cycle-specific manner by repression or activation (for review, see Zwicker et al., TiGS 14:3 (1997)); however, no cell cycle gene promoter containing a functional TATA box previously has been described.

The promoter of the murine cdc25B gene (SEQ ID NO: 7) consequently encompasses nucleotides ≦−950 to ≧+167, or part sequences of these nucleotide sequences, for example ≦−950 to ≧+1, −930 to +167, −720 to +167, −340 to +167, −180 to 167, −100 to +167, −80 to +167, −60 to +167 or −30 to +167, and/or corresponding part sequences up to +3 or +1.

Proceeding from the murine promoter sequences which have been found, it is straightforward for the skilled artisan to find non-murine cdc25B promoters which are homologous to the murine cdc25B promoter. This can be achieved by labeling, preferably radioactively labeling, the murine promoter and screening genomic DNA libraries obtained from mammalian cells by means of hybridization under stringent conditions.

Example 2

Preparation of Gene Constructs using Multiple Promoter Technology a) Preparation of an activator-responsive promoter unit The novel activator-responsive promoter unit comprises the following, different nucleotide sequences which succeed each other in the downstream direction:

Activator subunit A the promoter of the cdc25B gene (SEQ ID NO: 7) (nucleic acids −950 to +167)

the SV40 nuclear localization signal (SEQ ID NO: 9) (NLS) (SV40 large T, amino acids 126–132; PKKKRKV (SEQ ID NO: 9), Dingwall et al., *TIBS*, 16:478 (1991))

the acid transactivating domain (TAD) of HSV-1 VP16 (SEQ ID NO: 14) (amino acids 406 to 488; Triezenberg et al., *Genes Developm.*, 2:718 (1988); Triezenberg, *Curr. Opin. Gen. Developm.*, 5:190 (1995))

the cDNA for the cytoplasmic part of the CD4 glycoprotein (SEQ ID NO: 15) (amino acids 397–435; Simpson et al., *Oncogene*, 4:1141 (1989); Maddon et al., *Cell*, 93 (1985))

Activator subunit B the promoter of the cdc25C gene (SEQ ID NO: 19) (nucleic acids −290 bis +121; Zwicker et al., *EMBO J.*, 14:4514 (1995); Zwicker et al., *Nucl. Acids Res.*, 23:3822 (1995))

the SV40 nuclear localization signal (SEQ ID NO: 9) (NLS) (SV40 large T; amino acids 126–132 PKKKRKV; Dingwall et al., *TIBS*, 16:478 (1991))

the cDNA for the DNA-binding domain of the Gal4 protein (SEQ ID NO: 16) (amino acids 1 to 147, Chasman et al., *Mol. Cell. Biol.*, 10:2916 (1990))

the cDNA for the CD4-binding sequence of the p56 lck protein (SEQ ID NO: 17) (amino acids 1–71; Shaw et al., *Cell*, 59:627 (1989); Turner et al., *Cell*, 60:755 (1990); Perlmutter et al., *J. Cell. Biochem.*, 38:117 (1988))

Activator-responsive Promoters

10×the binding sequence for Gal4 binding protein having the nucleotide sequence (SEQ ID NO: 8) 5'-CGGACAATGTTGACCG-3' (Chasman et al., *Mol. Cell. Biol.* 10:2916 (1989))

the basal SV40 promoter (SEQ ID NO: 18) (nucleic acids 48 to 5191; Tooze (ed)., DNA Tumor Viruses (Cold Spring Harbor New York, N.Y., Cold Spring Harbor Laboratory) effector gene the cDNA for luciferase (Nordeen, *BioTechniques*, 6:454 (1988))

The described activator sequence functions as follows:

The cdc25B promoter regulates transcription of the combined cDNAs for the VP16 activation domain and the cytoplasmic part of CD4 (activation subunit A) in a cell cycle-specific manner. The cdc25C promoter regulates transcription of the combined cDNAs for the DNA-binding protein of Gal4 and the CD4-binding part of the p56 lck protein (activation subunit B) in a cell cycle-specific manner. The expression products of activator subunits A and B dimerize by the CD4 domain binding to the p56 lck domain. The dimeric protein constitutes a chimeric transcription factor for the activator-responsive promoter (DNA sequence for the Gal4-binding domains/the SV40 promoter) for transcription of the effector gene (=luciferase gene).

The individual components of the construct are linked together by way of suitable restriction sites which are added at the termini of the different elements during PCR amplification. The linking is effected using enzymes which are known to the skilled person and which are specific for the restriction sites, and DNA ligases. These enzymes can be obtained commercially.

The nucleotide construct which has been prepared in this way is cloned into the pXP2 plasmid vector (Nordeen, *BioTechniques*, 6:454 (1988)), which is then used directly, or in colloidal dispersion systems, for an in vivo application. 3T3 fibroblasts are transfected with the described plasmid using methods well known to the skilled artisan (Lucibello et al., *EMBO J.*, 14:132 (1995)) and the quantity of luciferase produced by the fibroblasts is measured as described by Herber et al. (*Oncogene*, 9:1295 (1994)) and Lucibello et al. (*EMBO J.*, 14:132 (1995)).

To check cell cycle specificity, the fibroblasts are synchronized in $G_0/G_1$ by removing serum over a period of 48 hours. The DNA content of the cells is determined in a fluorescence-activated cell sorter after staining with the dye Hoechst 33258 (Lucibello et al., *EMBO J.*, 14:132 (1995)).

The following results are obtained:

A marked increase in luciferase, as compared with non-transfected fibroblasts, can be ascertained in the transfected fibroblast. Proliferating fibroblasts (DNA>2S) form substantially more luciferase than do fibroblasts which are synchronized in $G_0/G_1$ (DNA=2 S). Consequently, the activator-responsive promoter unit which has been described leads to cell cycle-dependent expression of the reporter gene luciferase.

b) Preparation of a hybrid promoter

The novel hybrid promoter comprises the following different nucleotide sequences which succeed each other in the downstream direction:

the promoter of the cdc25B gene (SEQ ID NO: 7) (nucleic acids −950 to +167. The TATA box (nucleic acids TATATAA in position −30 to −23 are mutated to TGTATAA)).

the sequence GCCACC (Kodak, *J. Cell Biol.*, 108:229 (1989))

the cDNA for the immunoglobulin signal peptide (nucleotide sequence ≦63 to ≧107; Riechmann et al., *Nature* 332:323 (1988))

the cDNA for β-glucuronidase (SEQ ID NO: 12) (nucleotide sequence ≦93 to ≧1982; Oshima et al., *Proc. Nat'l Acad. Sci. USA* 84:685 (1987))

the promotor of the von Willebrand factor (vWF) gene (SEQ ID NO: 13) (nucleic acids −487 to +247; Jahroudi et al., *Mol. Cell Biol.* 14:999 (1994))

the gene for the TATA box-binding protein (nucleic acid sequence +1 to +1001, which is mutated in nucleic acids 862 (A replaced with T), 889 and 890 (GT replaced with AC) and 895 (C replaced with G) (Strubin et al., *Cell*, 68:721 (1992); Heard et al., *EMBO J.*, 12:3519 (1993)).

The individual components of the construct are linked by way of suitable restriction sites which are introduced at the termini of the different elements during PCR amplification. The linking is effected using enzymes which are known to the skilled person and which are specific for the restriction sites, and DNA ligases.

The nucleotide construct which has been prepared in this way is cloned into a pUC18/19 plasmid vector, which is used directly, or in colloidal dispersion systems, for an in-vivo application. Human umbilical cord endothelial cells and fibroblasts (Wi-38) which are being maintained in culture are transfected with the described plasmid using the method known to the skilled person (Lucibello et al., *EMBO J.*, 14:132 (1995)), and the quantity of β-glucuronidase which is produced by the endothelial cells is measured using 4-methylumbelliferyl-β-glucuronide as the substrate.

In order to check the cell cycle specificity, endothelial cells are synchronized in $G_0/G_1$ by removing methionine for a period of 48 hours. The DNA content of the cells is determined in a fluorescence-activated cell sorter after staining with Hoechst 33258 (Lucibello et al., *EMBO J.*, 14:132 (1995)).

The following results are obtained:

No increase in β-glucuronidase can be ascertained in transfected fibroblasts as compared with non-transfected fibroblasts. Transfected endothelial cells express substantially more β-glucuronidase than do non-transfected endothelial cells. Proliferating endothelial cells (DNA>2S; S=single set of chromosomes) secrete substantially more β-glucuronidase than do endothelial cells which are synchronized in $G_0/G_1$ (DNA=2S). Consequently, the multiple promoter unit which has been described leads to cell-specific, cell cycle-dependent expression of the structural gene β-glucuronidase.

c) Preparation of a multiple promoter having a nuclear retention signal (NRS) and a nuclear export factor (NEF)

The novel multiple promoter comprises the following different nucleotide sequences which succeed each other in the downstream direction:

- the promoter of the cdc25B gene (SEQ ID NO: 7) (nucleic acids −950 to +167)
- the sequence GCCACC; Seq. ID. No.: 1 (Kozak, *J. Cell Biol.*, 108:229 (1989))
- the cDNA for the immunoglobulin signal peptide (SEQ ID NO: 11) (nucleotide sequence ≦63 to ≧107; Riechmann et al., *Nature*, 332:323 (1988))
- the cDNA for β-glucuronidase (SEQ ID NO: 12) (nucleotide sequence ≦93 to ≧1982), Oshima et al., *Proc. Nat'l Acad. Sci. USA*, 84:685 (1987))
- the cDNA for HIV-1 virus RER as the nuclear retention signal (NRS) (nucleotide sequence 7357 to 7602; Ratner et al., *Nature*, 313:277 (1985); Malim et al., *Nature*, 338:254 (1989))
- the promotor of the von Willebrand factor (vWF) gene (SEQ ID NO: 13) (nucleic acid −487 to +247; Jahroudi et al., *Mol. Cell Biol.*, 14:999 (1994))
- the cDNA for HIV-1 virus REV as the nuclear export factor (NEF) (amino acid sequence 1–117; Ratner et al., *Nature*, 313:277 (1985))

The individual components of the construct are linked by way of suitable restriction sites which are introduced at the termini of the different elements during PCR amplification. The linking is effected using enzymes which are known to the skilled person and which are specific for the restriction sites, and DNA ligases. These enzymes can be obtained commercially. The nucleotide construct which has been prepared in this way is cloned into a pUC18/19 plasmid vector, which is used directly, or in colloidal dispersion systems, for an in vivo application. Human umbilical cord endothelial cells and fibroblasts (Wi-38) which are being maintained in culture are transfected with the described plasmid using the method known to the skilled person (Lucibello et al., *EMBO J.*, 14:132 (1995)), and the quantity of β-glucuronidase which is produced by the endothelial cells is measured using 4-methylumbelliferyl-β-glucuronide as the substrate.

In order to check the cell cycle specificity, endothelial cells are synchronized in $G_0/G_1$ by removing methionine over a period of 48 hours. The DNA content of the cells is determined in a fluorescence-activated cell sorter after staining with Hoechst 33258 (Lucibello et al., *EMBO J.*, 14:132 (1995)).

The following results are obtained:

No increase of β-glucuronidase can be ascertained in transfected fibroblasts as compared with non-transfected fibroblasts. Transfected endothelial cells express substantially more β-glucuronidase than do non-transfected endothelial cells. Proliferating endothelial cells (DNA>2S; S=single set of chromosomes) secrete substantially more β-glucuronidase than do endothelial cells which are synchronized in $G_0/G_1$ (DNA=2S). Consequently, the described multiple promoter unit leads to cell-specific, cell cycle-dependent expression of the structural gene β-glucuronidase.

Example 3

Application

An active compound according to the examples which have been described ensures, after local administration, for example at the site of the tumor, or after intracranial or subarachnoid administration, or systemic, preferably intravenous or intraarterial administration, that, as a result of the cell cycle specificity and endothelial cell specificity of the multiple promoter unit, it is in the main, if not exclusively, only proliferating endothelial cells which secrete β-glucuronidase. This β-glucuronidase cleaves an injectable, well-tolerated doxorubicin-β-glucuronide (Jacquesy et al., EPO 0 511 917 A1), into doxorubicin, which has a cytostatic effect. The doxorubicin inhibits proliferation of the endothelial cells and exerts a cytostatic effect on these cells and also on adjacent tumor cells. This results in inhibition of tumor growth.

The disclosure of all publications cited above are expressly incorporated herein by reference in their entireties to the same extent as if each were incorporated by reference individually. The disclosure of German Patent Application No. 19710643.9, for which benefit under 35 USC §119 is claimed, is expressly incorporated herein in its entirety.

What is claimed is:

1. An isolated promoter, wherein the promoter comprises the sequence depicted in Table 1 (SEQ ID NO: 7) or a functional part thereof.

2. A promoter according to claim 1, wherein the functional part comprises the TATA box, at least one Sp1-binding site and at least one NFY-binding site.

3. A promoter according to claim 1, which comprises the sequence encompassing the nucleotides from approx. −950 to approx. +167 of Table 1 (SEQ ID NO:7) or fragments thereof which still comprise all the functional cis-regulatory elements of the promoter sequence of the nucleotides from about −950 to about +167 as depicted in FIG. 6.

4. A promoter according to claim 1, which comprises the sequence encompassing the nucleotides from approx. −950 to approx. +3 of Table 1 (SEQ ID NO:7) or fragments thereof which still comprise all the functional cis-regulatory elements of the promoter sequence of the nucleotides from about −950 to +3 as depicted in FIG. 6.

5. A promoter according to claim 1, which comprises the sequence encompassing the nucleotides from about −930 to about +3 of Table 1 (SEQ ID NO:7), or fragments thereof which still comprise all the functional cis-regulatory elements of the promoter sequence of the nucleotides from approx. −930 to approx. +3 as depicted in FIG. 6.

6. A promoter according to claim 1, which comprises the sequence encompassing the nucleotides from about −720 to about +3 of Table 1 (SEQ ID NO:7) or fragments thereof which still comprise all the functional cis-regulatory elements of the promoter sequence of the nucleotides from about −720 to about +3 as depicted in FIG. 6.

7. A promoter according to claim 1, which comprises the sequence encompassing the nucleotides from about −340 to about 3 of Table 1 (SEQ ID NO:7) or fragments thereof which still comprise all the functional cis-regulatory elements of the promoter sequence of the nucleotides from about −340 to about +3 as depicted in FIG. 6.

8. A promoter according to claim 1, which comprises the sequence encompassing the nucleotides from about −180 to about +3 of Table 1 (SEQ ID NO: 7) or fragments thereof which still comprise all the functional cis-regulatory elements of the promoter sequence of the nucleotides from about −180 to about +3 as depicted in FIG. 6.

9. A promoter according to claim 1, which comprises the sequence encompassing the nucleotides from about −100 to about +3 of Table 1 (SEQ ID NO:7) or fragments thereof which still comprise all the functional cis-regulatory elements of the promoter sequence of the nucleotides from about −100 to about +3 as depicted in FIG. 6.

10. A promoter according to claim 1, which comprises the sequence encompassing the nucleotides from about −80 to about +3 of Table 1 (SEQ ID NO:7) or fragments thereof which still comprise all the functional cis-regulatory elements of the promoter sequence of the nucleotides from about −80 to about +3 as depicted in FIG. 6.

11. A promoter according to claim 1, which comprises the sequence encompassing the nucleotides from about −60 to about +3 of Table 1 (SEQ ID NO: 7) or fragments thereof which still comprise all the functional cis-regulatory elements of the promoter sequence of the nucleotides from about −60 to about +3 as depicted in FIG. 6.

12. A promoter according to claim 1, which comprises the sequence encompassing the nucleotides from about −30 to about +3 of Table 1 (SEQ ID NO:7) or fragments thereof which still comprise all the functional cis-regulatory elements of the promoter sequence of the nucleotides from about −30 to about +3 as depicted in FIG. 6.

13. A method for identifing cdc25B promoters, comprising screening a genomic DNA library using a labeled promoter, wherein said promoter is a promoter according to claim 1, and wherein said screening is carried out using hybridization under stringent conditions, whereby cdc25B promoters that hybridize to said labeled promoter are identified.

14. A nucleic acid construct comprising at least one promoter according to claim 1.

15. A nucleic acid construct, comprising a promoter according to claim 1 combined with at least one further activation sequence, wherein said further activation sequence is selected from the group consisting of non-specific, virus-specific, metabolically specific, cell-specific, cell cycle-specific and cell proliferation-dependent activation sequences.

16. A nucleic acid construct comprising in the orientation from 5' to 3':
   (a) a promoter according to claim 1, wherein said promoter comprises a TATA box that is mutated to TGTA,
   (b) the sequence GCCACC,
   (c) a cDNA for an immunoglobulin signal peptide (SEQ ID NO: 11),
   (d) a cDNA encoding β-glucuronidase (SEQ ID NO: 12),
   (e) a promoter of the von Willebrand Factor (vWF) gene (SEQ ID NO: 13), and
   (f) a cDNA for a TATA box-binding protein.

17. A nucleic acid construct comprising a promoter and a structural gene, further comprising at the 3' end of said structural gene (a) a nuclear retention signal, and (b) an additional promoter which activates transcription of a gene encoding a nuclear export factor, wherein the nuclear export factor binds to a mRNA transcript of the nuclear retention signal, wherein at least one of said promoters is a promoter according to claim 1.

18. A method for preparing a nucleic acid construct, comprising inserting a promoter according to claim 1 into a vector.

19. A promoter according to claim 2, further comprising at least one E2F-binding site.

20. A promoter according to claim 2, further comprising at least one E box.

21. A method according to claim 13, wherein said genomic DNA library is from mammalian cells.

22. A nucleic acid construct according to claim 14, further comprising a structural gene.

23. A nucleic acid construct according to claim 14, wherein said promoter is upstream of a structural gene.

24. A nucleic acid construct according to claim 14, wherein said promoter comprises at least one mutated transcription factor binding site.

25. A nucleic acid construct according to claim 14, wherein said nucleic acid is DNA.

26. A nucleic acid construct according to claim 14, wherein said nucleic acid construct is inserted into a vector.

27. A host cell comprising a nucleic acid construct according to claim 14.

28. A nucleic acid construct according to claim 15, wherein the further activation sequence is selected from the group consisting of promoters which are activated in endothelial cells, peritoneal cells, pleural cells, epithelial cells of the skin, cells of the lung, cells of the gastrointestinal tract, cells of the kidney and urine-draining pathways, muscle cells, connective tissue cells, hematopoietic cells, macrophages, lymphocytes, leukemia cells, tumor cells and glial cells; viral promoter sequences; promoter sequences which are activated by hypoxia; enhancer sequences that are activated by hypoxia, cell cycle-specific activation sequences of the genes encoding cdc25C, cyclin A, cdc2, E2F-1, B-myb and dihydrofolate reductase (DHFR), and binding sequences for transcription factors which appear or are activated in a cell proliferation-dependent manner.

29. A nucleic acid construct according to claim 15, wherein at least one of said promoter or activation sequences is included in an activator-responsive promoter unit.

30. A nucleic acid construct according to claim 16, comprising nucleotides 63 to 107 of the immunoglobulin signal peptide (SEQ ID NO: 11),
nucleotides 93 to 1982 of a glucuronidase cDNA (SEQ ID NO: 12), nucleotides −487 to +247 of a vWF gene promoter (SEQ ID NO: 13), and
a cDNA of a TATA box-binding protein cDNA, which is comutated such that it binds a mutated TATA box.

31. A nucleic acid construct according to claim 22, wherein said structural gene encodes an active compound selected from the group consisting of enzymes, fusion proteins, cytokines, chemokines, growth factors, receptors for cytokines, receptors for chemokines, receptors for growth factors, peptides and proteins having an antiproliferative or cytostatic or apoptotic effect, antibodies, antibody fragments, angiogenesis inhibitors, peptide hormones, coagulation factors, coagulation inhibitors, fibrinolytic proteins, peptides and proteins having an effect on blood circulation, blood plasma proteins, antigens of infectious agents, antigens of cells, antigens of tumors, thrombosis-inducing substances, complement-activating proteins, virus coat proteins and ribozymes.

32. A nucleic acid construct according to claim 24, wherein said at least one mutated transcription factor binding site is a TATA box.

33. A nucleic acid construct according to claim 24, further comprising (a) a first structural gene and (b) an additional promoter or enhancer sequence which activates the transcription of at least one second structural gene,
wherein said second structural gene encodes a transcription factor that activates the mutated promoter, and
wherein activation of said mutated promoter occurs via at least one mechanism selected from the group consisting of nonspecific activation, cell-specific activation, virus-specific activation, tetracycline activation, and cell cycle-specific activation.

34. A nucleic acid construct according to claim 26, wherein said vector is a plasmid vector or a viral vector.

35. A host cell according to claim 27, wherein said cell is an endotheliel cell.

36. A nucleic acid construct according to claim 29, wherein said activator-responsive promoter unit comprises:
(1) at least one activator subunit whose basal transcription is activated by a promoter or enhancer, and
(2) an activator-responsive promoter which is activated by the expression product of said activator subunit.

37. A nucleic acid construct according to claim 31, wherein said structural gene encodes an enzyme which cleaves a precursor of a drug into a drug.

38. A nucleic acid construct according to claim 31, wherein said structural gene encodes a ligand/active compound fusion protein or a ligand/enzyme fusion protein, wherein said ligand is selected from the group consisting of cytokines, growth factors, antibodies, antibody fragments, peptide hormones, mediators and cell adhesion proteins.

39. A nucleic acid construct according to claim 33, wherein said transcription factor binds to a mutated TATA box.

40. A nucleic acid construct according to claim 36, wherein said activator-responsive promoter unit comprises:
(a) a promoter of the cdc25B gene comprising the sequence as depicted in Table 1 (SEQ ID NO: 7) or a functional part thereof,
(b) the SV40 nuclear localization signal PKKKRKV (SEQ ID NO: 9),
(c) amino acids 406 to 488 of the HSV-1 VP16 acid transactivating domain (SEQ ID NO: 14), and
(d) a cDNA encoding amino acids 397–435 of the cytoplasmic portion of the CD4 glycoprotein (SEQ ID NO: 15)
and wherein said construct further comprises a second activator subunit, wherein said second activator subunit comprises:
(e) nucleic acids −290 to +121 of the promoter of the cdc25C gene (SEQ ID NO: 19),
(f) the SV40 nuclear localization signal PKKKRKV (SEQ ID NO: 9),
(g) amino acids 1 to 147 of the cDNA for the DNA-binding domain of the Gal4 protein (SEQ ID NO: 15) and
(h) amino acids 1–71 of the cDNA for the CD4-binding sequence of the p56 lck protein (SEQ ID NO: 17),
and wherein said nucleic acid construct further comprises
(g) up to about 10 copies of the activator-responsive promoter, wherein said activator-responsive promoter comprises (i) the 5'-CGGACAATGTTGACCG-3' binding sequence for Gal4 binding protein (SEQ ID NO: 8) and (ii) nucleotides 48 to 5191 of the basal SV40 promoter (SEQ ID NO: 18).

41. A nucleic acid construct according to claim 40, further comprising a structural gene which encodes (a) an active compound, (b) an enzyme or (c) a fusion protein which is composed of a ligand and an active compound or a ligand and an enzyme.

42. A process for isolating a murine cdc25B promoter, comprising screening a murine genomic phage library, obtained from the mouse strain 129FVJ, with a probe comprising a part of the sequence depicted in Table 1 (SEQ ID NO: 7) wherein said screening is carried out using hybridization under stringent conditions, whereby a cdc25B promoter that hybridizes to said labeled promoter is identified.

43. A process according to claim 42, wherein said probe comprises sequence SEQ ID NO: 4.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 68 base pairs
      (B) TYPE: nucleic acid
      (C) STRANDEDNESS: single
      (D) TOPOLOGY: linear

```
        (ii) MOLECULE TYPE: other nucleic acid
            (A) DESCRIPTION: /desc = "promoter"

(xi) SEQUENCE DESCRIPTION: SEQ ID NO:1:

AGCAGGTGTT GGGAGGCAGC AGGTGTTGGG AGGCAGCAGG TGTTGGGAGG CAGCAGGTGT        60

TGGGAGGC                                                                68

(2) INFORMATION FOR SEQ ID NO:2:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "promoter"

(xi) SEQUENCE DESCRIPTION: SEQ ID NO:2:

GGCCGATGGG CAGATAGAGG GGGCCGATGG GCAGATAGAG G                            41

(2) INFORMATION FOR SEQ ID NO:3:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:3:

GGAAGCAGAC CAGCTGGTCT GCTTCC                                             26

(2) INFORMATION FOR SEQ ID NO:4:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:4:

TCTAGCTAGC CTTTGCCCGC CCCGCCACGA TGGAGGTACC CCTGCAGAAG TCTGCGCCGG        60

GTTCAGCTCT CAGTCCTGCC                                                   80

(2) INFORMATION FOR SEQ ID NO:5:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide"

(xi) SEQUENCE DESCRIPTION: SEQ ID NO:5:

GGTCATTCAA AATGAGCAGT TACCATAAAA CGCTTCCGAT CCTTACCAGT GAGGCTTGCT        60

GGAACACAGT CCGGTGCTG                                                    79

(2) INFORMATION FOR SEQ ID NO:6:
```

(i) SEQUENCE CHARACTERISTICS:
    (A) LENGTH: 80 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:6:

```
GTTAAAGAAG CATTGTTATT ATGGGGAGGG GGGAGCAACC TCTGGGTTCA GAATCTACAT    60

ATGCTGGAAG GCCCCAATGA                                                80
```

(2) INFORMATION FOR SEQ ID NO:7:

(i) SEQUENCE CHARACTERISTICS:
       (A) LENGTH: 1122 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "promoter"

(xi) SEQUENCE DESCRIPTION: SEQ ID NO:7:

```
AGTTCTCAAC TGCCCACTAG GTCCTTCCCA GCTCATTCCA GGAAAACAGA CTCAGCTGCA    60

AGGTGATTAG GTCATTAGAA AACGCTCATT GTAAACTAAT AGCAAATTCA GCCTCTTTCA   120

CCTTCAAAGA AACACTAAAT ATGGTGCTAT TAACCCCAAA TTAGCCAAGT GGGTGTGAGA   180

TTTTTTTCCC CCTAGTTGGG TTCTCTGGTG GCATGTCCCA ACTGTGTGTT GCAGAAATCA   240

TTGCCTAAAT CTAAGCGTCT AATTCTCAGG AGAATAGGCT CAGTGGGGTC ACATCTAAAC   300

TCTGGTGCCC CAGAACCCAG CAGTTCCACT GTGCCTCGCA AAGGGCTGCC AGCAAACGAC   360

TGCAGCTGCT CTGTGAGGTC CAGGGGCGAT GACAGGAGGC TGCACCATCA GCGGAGTCCC   420

TGAGGGAGCT TCTATGTCTC TGCCACTCAA CCGAACCTGT GACCTTAAAC GAGTTAAAGA   480

GCTTTTCAAC GCTGGGGTCT GTGAACTGGA CAGGGAACGC AGTGCTCACA GCATACTTGG   540

CAAACGTCCT GGGCTCAAGC AGAGCGTCGC ACCGTCCCTT ACTGATGAAC GTGCATGATG   600

GTAAACGTTG AGGGCTCCTT ATGAGGCCAC CTTAGGGGAT GACTACTCCC TCTGAGGGTA   660

GAGGGCTGCT CCCACCTCCA AACCCTGTTC CAGGAGGCAA TATCCTGGAG GCCCAGGATT   720

CTCGCGTCAA TGGGAGCGGG CGGGGCCGGG GCGGTACGTG TGGGGCAGGG GGTTAACCCA   780

ACTCCCCGAG TCACCCTAAG AAGCCAGGCG AGCAGAAGTA GCTGGTCCAG CCTCAGCCTC   840

AGCCCCGCCC TTGGTCCCGC CCTCCCGGAA CCGGCGCCCC CATTGGTGGC GTCTGGCGGC   900

GCTGCCGCTG TTATTTTTCG AATATATAAG GAGGTGGAGG TGGCAGCTGC CCAGCTCGGC   960

GTCCTCCCCT CCCTTCCTCC CCACATCCCT CTCCTCACTC CCAGGCCCAT TGCTCTTCCT  1020

CCCTCCCTTC CCTCCCTCCT TCCCCTCACC CCAGGCTCAC TCTCGGAGCT GAGCCAGCTG  1080

GGTCGGCGTC TGCTGGCCGC TGTACTGTGG CCCTCTAGCT AG                    1122
```

(2) INFORMATION FOR SEQ ID NO:8:

(i) SEQUENCE CHARACTERISTICS:
       (A) LENGTH: 16 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "oligonucleotide"

(xi) SEQUENCE DESCRIPTION: SEQ ID NO:8:

CGGACAATGT TGACCG                                                    16

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Pro Lys Lys Lys Arg Lys Val
1               5

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:10:

GGAAGCAGAC CACGTGGTCT GCTTCC                                         26

(2) INFORMATION FOR SEQ ID NO:11:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ACAAACAGAA AAACATGAGA TCACAGTTCT CTCTACAGTT ACTGAGCACA CAGGACCTCA     60

ATGAAGTTGT GGCTGAACTG GATTTTCCTT TTAACACTTT TAAATGGTAT CCAGTGTGAG    120

GTGAAACTGT TGGAATCTGG AGGAGGCTTG GTACAGCCGG GGGGTTCTAT GAGACTCTCC    180

TGTGCAGGTT CTGGATTCAC CTTCACTGAT TTCTACATGA ACTGGATCCG CCAGCCTGCA    240

GGGAAGGCAC CTGAGTGGCT GGGTTTTATT AGAGACAAAG CTAAAGGTTA CAACAGAG      300

TACAATCCAT CTGTGAAGGG GCGGTTCACC ATCTCCAGAG ATAATACCCA AAACATGCTC    360

TATCTTCAAA TGAACACCCT AAGAGCTGAG GACACTGCCA CTTACTACTG TGCAAGAGAG    420

GGCCACACTG CTGCTCCTTT TGATTACTGG GGCCAAGGAG TCATGGTCAC AGTCTCCTCA    480

(2) INFORMATION FOR SEQ ID NO:12:

(i) SEQUENCE CHARACTERISTICS:
        (A) LENGTH: 2191 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
GGTGGCCGAG CGGGGGACCG GGAAGCATGG CCCGGGGGTC GGCGGTTGCC TGGGCGGCGC      60

TCGGGCCGTT GTTGTGGGGC TGCGCGCTGG GGCTGCAGGG CGGGATGCTG TACCCCCAGG     120

AGAGCCCGTC GCGGGAGTGC AAGGAGCTGG ACGGCCTCTG GAGCTTCCGC GCCGACTTCT     180

CTGACAACCG ACGCCGGGGC TTCGAGGAGC AGTGGTACCG GCGGCCGCTG TGGGAGTCAG     240

GCCCCACCGT GGACATGCCA GTTCCCTCCA GCTTCAATGA CATCAGCCAG GACTGGCGTC     300

TGCGGCATTT TGTCGGCTGG GTGTGGTACG AACGGGAGGT GATCCTGCCG GAGCGATGGA     360

CCCAGGACCT GCGCACAAGA GTGGTGCTGA GGATTGGCAG TGCCCATTCC TATGCCATCG     420

TGTGGGTGAA TGGGGTCGAC ACGCTAGAGC ATGAGGGGG CTACCTCCCC TTCGAGGCCG      480

ACATCAGCAA CCTGGTCCAG GTGGGGCCCC TGCCCTCCCG GCTCCGAATC ACTATCGCCA     540

TCAACAACAC ACTCACCCCC ACCACCCTGC CACCAGGGAC CATCCAATAC CTGACTGACA     600

CCTCCAAGTA TCCCAAGGGT TACTTTGTCC AGAACACATA TTTTGACTTT TTCAACTACG     660

CTGGACTGCA GCGGTCTGTA CTTCTGTACA CGACACCCAC CACCTACATC GATGACATCA     720

CCGTCACCAC CAGCGTGGAG CAAGACAGTG GGCTGGTGAA TTACCAGATC TCTGTCAAGG     780

GCAGTAACCT GTTCAAGTTG GAAGTGCGTC TTTTGGATGC AGAAAACAAA GTCGTGGCGA     840

ATGGGACTGG GACCCAGGGC CAACTTAAGG TGCCAGGTGT CAGCCTCTGG TGGCCGTACC     900

TGATGCACGA ACGCCCTGCC TATCTGTATT CATTGGAGGT GCAGCTGACT GCACAGACGT     960

CACTGGGGCC TGTGTCTGAC TTCTACACAC TCCCTGTGGG GATCCGCACT GTGGCTGTCA    1020

CCAAGAGCCA GTTCCTCATC AATGGGAAAC CTTTCTATTT CCACGGTGTC AACAAGCATG    1080

AGGATGCGGA CATCCGAGGG AAGGGCTTCG ACTGGCCGCT GCTGGTGAAG GACTTCAACC    1140

TGCTTCGCTG GCTTGGTGCC AACGCTTTCC GTACCAGCCA CTACCCCTAT GCAGAGGAAG    1200

TGATGCAGAT GTGTGACCGC TATGGGATTG TGGTCATCGA TGAGTGTCCC GGCGTGGGCC    1260

TGGCGCTGCC GCAGTTCTTC AACAACGTTT CTCTGCATCA CCACATGCAG GTGATGGAAG    1320

AAGTGGTGCG TAGGGACAAG AACCACCCCG CGGTCGTGAT GTGGTCTGTG GCCAACGAGC    1380

CTGCGTCCCA CCTAGAATCT GCTGGCTACT ACTTGAAGAT GGTGATCGCT CACACCAAAT    1440

CCTTGGACCC CTCCCGGCCT GTGACCTTTG TGAGCAACTC TAACTATGCA GCAGACAAGG    1500

GGGCTCCGTA TGTGGATGTG ATCTGTTTGA ACAGCTACTA CTCTTGGTAT CACGACTACG    1560

GCACCTGGA GTTGATTCAG CTGCAGCTGG CCACCCAGTT TGAGAACTGG TATAAGAAGT    1620

ATCAGAAGCC CATTATTCAG AGCGAGTATG GAGCAGAAAC GATTGCAGGG TTTCACCAGG    1680

ATCCACCTCT GATGTTCACT GAAGAGTACC AGAAAAGTCT GCTAGAGCAG TACCATCTGG    1740

GTCTGGATCA AAAACGCAGA AAATATGTGG TTGGAGAGCT CATTTGGAAT TTTGCCGATT    1800

TCATGACTGA ACAGTCACCG ACGAGAGTGC TGGGGAATAA AAAGGGGATC TTCACTCGGC    1860

AGAGACAACC AAAAAGTGCA GCGTTCCTTT TGCGAGAGAG ATACTGGAAG ATTGCCAATG    1920

AAACCAGGTA TCCCCACTCA GTAGCCAAGT CACAATGTTT GGAAAACAGC CCGTTTACTT    1980

GAGCAAGACT GATACCACCT GCGTGTCCCT TCCTCCCCGA GTCAGGGCGA CTTCACAGCC    2040

AGCAGAACAA GTGCCTCCTG GACTGTTCAC GGCAGACCAG AACGTTTCTG GCCTGGGTTT    2100

TGTGGTCATC TATTCTAGCA GGGAACACTA AAGGTGGAAA TAAAGATTT TCTATTATGG     2160

AAATAAAGAG TTGGCATGAA AGTCGCTACT G                                   2191

(2) INFORMATION FOR SEQ ID NO:13:

(i) SEQUENCE CHARACTERISTICS:
        (A) LENGTH: 1080 base pairs
```

(B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
GGGTGCTTGT CTCAGTGCCT GGAATCCCAG CACGAGAGTC ATCTTCCCCC CACCGCTGCC      60

CATTGCATCA GTTACTTATT TTAGTAGGAA TTAGTTTAGC AGATGGTGTT GAGAATTAGG     120

CTTTTGGGAA TGGAGGCTG GGAAGAAGAA TTGTGTGTGT GTGTGTGTGT GTGTGTGTGT      180

GTGTGTGTGT AAGATCAGGG TACCAGAAGT GGGTGGAAAT GTCCTTGAGA ATTAGAATTA     240

TTAGAATGTA GCAACAGTAG AAGTATTAGA CTCAAACCAT CACTCCCCAC CTTCACCATT     300

TTACAAAGGC TTAGGCTTGT GGCCAAGACC TTCATCTTTA GCCGATCCAT TCAACCCTGG     360

CCAGGATCCA AATGGACTGT TTTTGTCAGG GCCAGGACCG GATCCTTCAT ACCTGGGGTG     420

CATAGGAAGT GTTAGTACTC CCCTTCCTCC AAACACAGCA GCAAAATTGG CTCAGGTTGA     480

GGTGTTTTTC TCAACTTCCC TGGAGTCCAG CCCTGGAAGC TGGATCAGGA AGCTGTGTTG     540

TTCTACTGTG ATTCCCCCTG GCCTGTATCA GCTTGCCCTG AAACAACCAG CATTCCTGGT     600

TATCCCACAC AGGTGGGGCA CTCTAGGAAG ACCAGGGATC AAGTGTGGGG GTGTAGGGAT     660

AGGGGGTGTT TGGGGAGGGC AAGGCAGTTA ATTAAGGCAG CTGCCAGGAG GTCTCCCTCC     720

AAACTCTACA AAGCTTTATC AGCTTGGAGG TACTTCTAAT ACCATTTCCT TTCATTGTTT     780

CCTTTTGGTA ATTAAAAGGA GGCCAATCCC CTGTTGTGGC AGCTCACAGC TATTGTGGTG     840

GGAAAGGGAG GGTGGTTGGT GGATGTCACA GCTTGGGCTT TATCTCCCCC AGCAGTGGGG     900

ACTCCACAGC CCCTGGGCTA CATAACAGCA AGACAGTCCG GAGCTGTAGC AGACCTGATT     960

GAGCCTTTGC AGCAGCTGAG AGCATGGCCT AGGGTGGGCG GCACCATTGT CCAGCAGCTG    1020

AGTTTCCCAG GGACCTTGGA GATAGCCGCA GCCCTCATTT GCAGGGGAAG GTATGGCCTT    1080
```

(2) INFORMATION FOR SEQ ID NO:14:

(i) SEQUENCE CHARACTERISTICS:
        (A) LENGTH: 490 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

```
Met Asp Leu Leu Val Asp Glu Leu Phe Ala Asp Met Asn Ala Asp Gly
1               5                   10                  15

Ala Ser Pro Pro Pro Arg Pro Ala Gly Gly Pro Lys Asn Thr Pro
            20                  25                  30

Ala Ala Pro Pro Leu Tyr Ala Thr Gly Arg Leu Ser Gln Ala Gln Leu
        35                  40                  45

Met Pro Ser Pro Pro Met Pro Val Pro Pro Ala Leu Phe Asn Arg
    50                  55                  60

Leu Leu Asp Asp Leu Gly Phe Ser Ala Gly Pro Ala Leu Cys Thr Met
65                  70                  75                  80

Leu Asp Thr Trp Asn Glu Asp Leu Phe Ser Ala Leu Pro Thr Asn Ala
                85                  90                  95

Asp Leu Tyr Arg Glu Cys Lys Phe Leu Ser Thr Leu Pro Ser Asp Val
                100                 105                 110

Val Glu Trp Gly Asp Ala Tyr Val Pro Glu Arg Thr Gln Ile Asp Ile
```

```
            115                 120                 125
Arg Ala His Gly Asp Val Ala Phe Pro Thr Leu Pro Ala Thr Arg Asp
        130                 135                 140

Gly Leu Gly Leu Tyr Tyr Glu Ala Leu Ser Arg Phe Phe His Ala Glu
145                 150                 155                 160

Leu Arg Ala Arg Glu Glu Ser Tyr Arg Thr Val Leu Ala Asn Phe Cys
                165                 170                 175

Ser Ala Leu Tyr Arg Tyr Leu Arg Ala Ser Val Arg Gln Leu His Arg
            180                 185                 190

Gln Ala His Met Arg Gly Arg Asp Arg Asp Leu Gly Glu Met Leu Arg
        195                 200                 205

Ala Thr Ile Ala Asp Arg Tyr Tyr Arg Glu Thr Ala Arg Leu Ala Arg
210                 215                 220

Val Leu Phe Leu His Leu Tyr Leu Phe Leu Thr Arg Glu Ile Leu Trp
225                 230                 235                 240

Ala Ala Tyr Ala Glu Gln Met Met Arg Pro Asp Leu Phe Asp Cys Leu
                245                 250                 255

Cys Cys Asp Leu Glu Ser Trp Arg Gln Leu Ala Gly Leu Phe Gln Pro
            260                 265                 270

Phe Met Phe Val Asn Gly Ala Leu Thr Val Arg Gly Val Pro Ile Glu
        275                 280                 285

Ala Arg Arg Leu Arg Glu Leu Asn His Ile Arg Glu His Leu Asn Leu
290                 295                 300

Pro Leu Val Arg Ser Ala Ala Thr Glu Glu Pro Gly Ala Pro Leu Thr
305                 310                 315                 320

Thr Pro Pro Thr Leu His Gly Asn Gln Ala Arg Ala Ser Gly Tyr Phe
                325                 330                 335

Met Val Leu Ile Arg Ala Lys Leu Asp Ser Tyr Ser Ser Phe Thr Thr
            340                 345                 350

Ser Pro Ser Glu Ala Val Met Arg Glu His Ala Tyr Ser Arg Ala Arg
        355                 360                 365

Thr Lys Asn Asn Tyr Gly Ser Thr Ile Glu Gly Leu Leu Asp Leu Pro
370                 375                 380

Asp Asp Asp Ala Pro Glu Glu Ala Gly Leu Ala Ala Pro Arg Leu Ser
385                 390                 395                 400

Phe Leu Pro Ala Gly His Thr Arg Arg Leu Ser Thr Ala Pro Pro Thr
                405                 410                 415

Asp Val Ser Leu Gly Asp Glu Leu His Leu Asp Gly Glu Asp Val Ala
            420                 425                 430

Met Ala His Ala Asp Ala Leu Asp Asp Phe Asp Leu Asp Met Leu Gly
        435                 440                 445

Asp Gly Asp Ser Pro Gly Pro Gly Phe Thr Pro His Asp Ser Ala Pro
450                 455                 460

Tyr Gly Ala Leu Asp Met Ala Asp Phe Glu Phe Glu Gln Met Phe Thr
465                 470                 475                 480

Asp Ala Leu Gly Ile Asp Glu Tyr Gly Gly
                485                 490
```

(2) INFORMATION FOR SEQ ID NO:15:

(i) SEQUENCE CHARACTERISTICS:
        (A) LENGTH: 458 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Leu Gly Lys
            20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400
```

Val Leu Gly Gly Val Ala Gly Leu Leu Phe Ile Gly Leu Gly Ile
                405                 410                 415

Phe Phe Cys Val Arg Cys Arg His Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
450                 455

(2) INFORMATION FOR SEQ ID NO:16:

(i) SEQUENCE CHARACTERISTICS:
        (A) LENGTH: 881 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
            35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
            115                 120                 125

Ala Thr Ser Ser Ser Glu Glu Ser Ser Asn Lys Gly Gln Arg Gln Leu
130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
            180                 185                 190

Asn Asn Gly Phe Phe Gly Asp Gly Ser Leu Leu Cys Ile Leu Arg Ser
            195                 200                 205

Ile Gly Phe Lys Pro Glu Asn Tyr Thr Asn Ser Asn Val Asn Arg Leu
210                 215                 220

Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
                245                 250                 255

Ile Val His Ser Pro Thr Leu Met Met Leu Tyr Asn Asn Gln Ile Glu
            260                 265                 270

Ile Ala Ser Lys Asp Gln Trp Gln Ile Leu Phe Asn Cys Ile Leu Ala
            275                 280                 285

-continued

```
Ile Gly Ala Trp Cys Ile Glu Gly Glu Ser Thr Asp Ile Asp Val Phe
290                 295                 300

Tyr Tyr Gln Asn Ala Lys Ser His Leu Thr Ser Lys Val Phe Glu Ser
305                 310                 315                 320

Gly Ser Ile Ile Leu Val Thr Ala Leu His Leu Leu Ser Arg Tyr Thr
                325                 330                 335

Gln Trp Arg Gln Lys Thr Asn Thr Ser Tyr Asn Phe His Ser Phe Ser
            340                 345                 350

Ile Arg Met Ala Ile Ser Leu Gly Leu Asn Arg Asp Leu Pro Ser Ser
        355                 360                 365

Phe Ser Asp Ser Ser Ile Leu Glu Gln Arg Arg Ile Trp Trp Ser
370                 375                 380

Val Tyr Ser Trp Glu Ile Gln Leu Ser Leu Leu Tyr Gly Arg Ser Ile
385                 390                 395                 400

Gln Leu Ser Gln Asn Thr Ile Ser Phe Pro Ser Ser Val Asp Asp Val
                405                 410                 415

Gln Arg Thr Thr Thr Gly Pro Thr Ile Tyr His Gly Ile Ile Glu Thr
            420                 425                 430

Ala Arg Leu Leu Gln Val Phe Thr Lys Ile Tyr Glu Leu Asp Lys Thr
        435                 440                 445

Val Thr Ala Glu Lys Ser Pro Ile Cys Ala Lys Lys Cys Leu Met Ile
450                 455                 460

Cys Asn Glu Ile Glu Glu Val Ser Arg Gln Ala Pro Lys Phe Leu Gln
465                 470                 475                 480

Met Asp Ile Ser Thr Thr Ala Leu Thr Asn Leu Leu Lys Glu His Pro
                485                 490                 495

Trp Leu Ser Phe Thr Arg Phe Glu Leu Lys Trp Lys Gln Leu Ser Leu
            500                 505                 510

Ile Ile Tyr Val Leu Arg Asp Phe Phe Thr Asn Phe Thr Gln Lys Lys
        515                 520                 525

Ser Gln Leu Glu Gln Asp Gln Asn Asp His Gln Ser Tyr Glu Val Lys
530                 535                 540

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
                565                 570                 575

Asn Cys Ser Tyr Tyr Leu Phe Asn Ala Val Leu Val Pro Ile Lys Thr
            580                 585                 590

Leu Leu Ser Asn Ser Lys Ser Asn Ala Glu Asn Asn Glu Thr Ala Gln
        595                 600                 605

Leu Leu Gln Gln Ile Asn Thr Val Leu Met Leu Leu Lys Lys Leu Ala
610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
                645                 650                 655

Ile Ser Tyr Asn Asn Ser Asn Gly Ser Ala Ile Lys Asn Ile Val Gly
            660                 665                 670

Ser Ala Thr Ile Ala Gln Tyr Pro Thr Leu Pro Glu Glu Asn Val Asn
        675                 680                 685

Asn Ile Ser Val Lys Tyr Val Ser Pro Gly Ser Val Gly Pro Ser Pro
690                 695                 700
```

-continued

```
Val Pro Leu Lys Ser Gly Ala Ser Phe Ser Asp Leu Val Lys Leu Leu
705                 710                 715                 720

Ser Asn Arg Pro Pro Ser Arg Asn Ser Pro Val Thr Ile Pro Arg Ser
            725                 730                 735

Thr Pro Ser His Arg Ser Val Thr Pro Phe Leu Gly Gln Gln Gln Gln
            740                 745                 750

Leu Gln Ser Leu Val Pro Leu Thr Pro Ser Ala Leu Phe Gly Gly Ala
            755                 760                 765

Asn Phe Asn Gln Ser Gly Asn Ile Ala Asp Ser Ser Leu Ser Phe Thr
770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Ser Asn Val His Asp Asn
            805                 810                 815

Phe Met Asn Asn Glu Ile Thr Ala Ser Lys Ile Asp Asp Gly Asn Asn
            820                 825                 830

Ser Lys Pro Leu Ser Pro Gly Trp Thr Asp Gln Thr Ala Tyr Asn Ala
            835                 840                 845

Phe Gly Ile Thr Thr Gly Met Phe Asn Thr Thr Thr Met Asp Asp Val
850                 855                 860

Tyr Asn Tyr Leu Phe Asp Asp Glu Asp Thr Pro Pro Asn Pro Lys Lys
865                 870                 875                 880

Glu (2) INFORMATION FOR SEQ ID NO:17:

(i) SEQUENCE CHARACTERISTICS:
        (A) LENGTH: 509 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
            35                  40                  45

Val Thr Tyr Glu Gly Ser Asn Pro Ala Ser Pro Leu Gln Asp Asn
50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
            85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
            115                 120                 125

Phe Lys Asn Leu Ser Arg Lys Asp Ala Glu Arg Gln Leu Leu Ala Pro
            130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
```

```
                        165                 170                 175
Val Val Lys His Tyr Lys Ile Arg Asn Leu Asp Asn Gly Gly Phe Tyr
                180                 185                 190

Ile Ser Pro Arg Ile Thr Phe Pro Gly Leu His Glu Leu Val Arg His
            195                 200                 205

Tyr Thr Asn Ala Ser Asp Gly Leu Cys Thr Arg Leu Ser Arg Pro Cys
        210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
        355                 360                 365

Asn Ile Leu Val Ser Asp Thr Leu Ser Cys Lys Ile Ala Asp Phe Gly
    370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505
```

(2) INFORMATION FOR SEQ ID NO:18:

(i) SEQUENCE CHARACTERISTICS:
        (A) LENGTH: 5183 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
GCCTCGGCCT CTGCATAAAT AAAAAAAATT AGTCAGCCAT GGGGCGGAGA ATGGGCGGAA      60
```

-continued

| | |
|---|---|
| CTGGGCGGAG TTAGGGGCGG GATGGGCGGA GTTAGGGGCG GGACTATGGT TGCTGACTAA | 120 |
| TTGAGATGCA TGCTTTGCAT ACTTCTGCCT GCTGGGGAGC CTGGGGACTT TCCACACCTG | 180 |
| GTTGCTGACT AATTGAGATG CATGCTTTGC ATACTTCTGC CTGCTGGGGA GCCTGGGGAC | 240 |
| TTTCCACACC CTAACTGACA CACATTCCAC AGCTGGTTCT TTCCGCCTCA GAAGGTACCT | 300 |
| AACCAAGTTC CTCTTTCAGA GGTTATTTCA GGCCATGGTG CTGCGCCGGC TGTCACGCCA | 360 |
| GGCCTCCGTT AAGGTTCGTA GGTCATGGAC TGAAAGTAAA AAAACAGCTC AACGCCTTTT | 420 |
| TGTGTTTGTT TTAGAGCTTT TGCTGCAATT TTGTGAAGGG GAAGATACTG TTGACGGGAA | 480 |
| ACGCAAAAAA CCAGAAAGGT TAACTGAAAA ACCAGAAAGT TAACTGGTAA GTTTAGTCTT | 540 |
| TTTGTCTTTT ATTTCAGGTC CATGGGTGCT GCTTTAACAC TGTTGGGGGA CCTAATTGCT | 600 |
| GCCGCTGCTG CAATTGAAGT GCAACTTGCA TCTGTTGCTA CTGTTGAAGG CCTAACAACC | 660 |
| TCTGAGGCAA TTGCTGCTAT AGGCCTCACT CCACAGGCCT ATGCTGTGAT ATCTGGGGCT | 720 |
| CCTGCTGCTA TAGCTGGATT TGCAGCTTTA CTGCAAACTG TGACTGGTGT GAGCGCTGTT | 780 |
| GCTCAAGTGG GGTATAGATT TTTTAGTGAC TGGGATCACA AAGTTTCTAC TGTTGGTTTA | 840 |
| TATCAACAAC CAGGAATGGC TGTAGATTTG TATAGGCCAG ATGATTACTA TGATATTTTA | 900 |
| TTTCCTGGAG TACAAACCTT TGTTCACAGT GTTCAGTATC TTGACCCCAG ACATTGGGGT | 960 |
| CCAACACTTT TTAATGCCAT TTCTCAAGCT TTTTGGCGTG TAATACAAAA TGACATTCCT | 1020 |
| AGGCTCACCT CACAGGAGCT TGAAAGAAGA ACCCAAAGAT ATTTAAGGGA CAGTTTGGCA | 1080 |
| AGGTTTTTAG AGGAAACTAC TTGGACAGTA ATTAATGCTC CTGTTAATTG GTATAACTCT | 1140 |
| TTACAAGATT ACTACTCTAC TTTGTCTCCC ATTAGGCCTA CAATGGTGAG ACAAGTAGCC | 1200 |
| AACAGGGAAG GGTTGCAAAT ATCATTTGGG CACACCTATG ATAATATTGA TGAAGCAGAC | 1260 |
| AGTATTCAGC AAGTAACTGA GAGGTGGGAA GCTCAAAGCC AAAGTCCTAA TGTGCAGTCA | 1320 |
| GGTGAATTTA TTGAAAAATT TGAGGCTCCT GGTGGTGCAA ATCAAAGAAC TGCTCCTCAG | 1380 |
| TGGATGTTGC CTTTACTTCT AGGCCTGTAC GGAAGTGTTA CTTCTGCTCT AAAAGCTTAT | 1440 |
| GAAGATGGCC CCAACAAAAA GAAAAGGAAG TTGTCCAGGG GCAGCTCCCA AAAAACCAAA | 1500 |
| GGAACCAGTG CAAGTGCCAA AGCTCGTCAT AAAAGGAGGA ATAGAAGTTC TAGGAGTTAA | 1560 |
| AACTGGAGTA GACAGCTTCA CTGAGGTGGA GTGCTTTTTA AATCCTCAAA TGGGCAATCC | 1620 |
| TGATGAACAT CAAAAAGGCT TAAGTAAAAG CTTAGCAGCT GAAAAACAGT TTACAGATGA | 1680 |
| CTCTCCAGAC AAAGAACAAC TGCCTTGCTA CAGTGTGGCT AGAATTCCTT TGCCTAATTT | 1740 |
| AAATGAGGAC TTAACCTGTG GAAATATTTT GATGTGGGAA GCTGTTACTG TTAAAACTGA | 1800 |
| GGTTATTGGG GTAACTGCTA TGTTAAACTT GCATTCAGGG ACACAAAAAA CTCATGAAAA | 1860 |
| TGGTGCTGGA AAACCCATTC AAGGGTCAAA TTTTCATTTT TTTGCTGTTG GTGGGGAACC | 1920 |
| TTTGGAGCTG CAGGGTGTGT TAGCAAACTA CAGGACCAAA TATCCTGCTC AAACTGTAAC | 1980 |
| CCCAAAAAAT GCTACAGTTG ACAGTCAGCA GATGAACACT GACCACAAGG CTGTTTTGGA | 2040 |
| TAAGGATAAT GCTTATCCAG TGGAGTGCTG GGTTCCTGAT CCAAGTAAAA ATGAAAACAC | 2100 |
| TAGATATTTT GGAACCTACA CAGGTGGGGA AAATGTGCCT CCTGTTTTGC ACATTACTAA | 2160 |
| CACAGCAACC ACAGTGCTTC TTGATGAGCA GGGTGTTGGG CCCTTGTGCA AAGCTGACAG | 2220 |
| CTTGTATGTT TCTGCTGTTG ACATTTGTGG GCTGTTTACC AACACTTCTG GAACACAGCA | 2280 |
| GTGGAAGGGA CTTCCCAGAT ATTTTAAAAT TACCCTTAGA AAGCGGTCTG TGAAAAACCC | 2340 |
| CTACCCAATT TCCTTTTTGT TAAGTGACCT AATTAACAGG AGGACACAGA GGGTGGATGG | 2400 |

```
GCAGCCTATG ATTGGAATGT CCTCTCAAGT AGAGGAGGTT AGGGTTTATG AGGACACAGA    2460

GGAGCTTCCT GGGGATCCAG ACATGATAAG ATACATTGAT GAGTTTGGAC AAACCACAAC    2520

TAGAATGCAG TGAAAAAAAT GCTTTATTTG TGAAATTTGT GATGCTATTG CTTTATTTGT    2580

AACCATTATA AGCTGCAATA AACAAGTTAA CAACAACAAT TGCATTCATT TTATGTTTCA    2640

GGTTCAGGGG GAGGTGTGGG AGGTTTTTTA AAGCAAGTAA AACCTCTACA AATGTGGTAT    2700

GGCTGATTAT GATCATGAAC AGACTGTGAG GACTGAGGGG CCTGAAATGA GCCTTGGGAC    2760

TGTGAATCAA TGCCTGTTTC ATGCCCTGAG TCTTCCATGT TCTTCTCCCC ACCATCTTCA    2820

TTTTTATCAG CATTTTCCTG GCTGTCTTCA TCATCATCAT CACTGTTTCT TAGCCAATCT    2880

AAAACTCCAA TTCCCATAGC CACATTAAAC TTCATTTTTT GATACACTGA CAAACTAAAC    2940

TCTTTGTCCA ATCTCTCTTT CCACTCCACA ATTCTGCTCT GAATACTTTG AGCAAACTCA    3000

GCCACAGGTC TGTACCAAAT TAACATAAGA AGCAAAGCAA TGCCACTTTG AATTATTCTC    3060

TTTTCTAACA AAAACTCACT GCGTTCCAGG CAATGCTTTA AATAATCTTT GGGCCTAAAA    3120

TCTATTTGTT TTACAAATCT GGCCTGCAGT GTTTTAGGCA CACTGTACTC ATTCATGGTG    3180

ACTATTCCAG GGGGAAATAT TTGAGTTCTT TTATTTAGGT GTTTCTTTTC TAAGTTTACC    3240

TTAACACTGC CATCCAAATA ATCCCTTAAA TTGTCCAGGT TATTAATTCC CTGACCTGAA    3300

GGCAAATCTC TGGACTCCCC TCCAGTGCCC TTTACATCCT CAAAAACTAC TAAAAACTGG    3360

TCAATAGCTA CTCCTAGCTC AAAGTTCAGC CTGTCCAAGG GCAAATTAAC ATTTAAAGCT    3420

TTCCCCCCAC ATAATTCAAG CAAAGCAGCT GCTAATGTAG TTTTACCACT ATCAATTGGT    3480

CCTTTAAACA GCCAGTATCT TTTTTTAGGA ATGTTGTACA CCATGCATTT TAAAAAGTCA    3540

TACACCACTG AATCCATTTT GGGCAACAAA CAGTGTAGCC AAGCAACTCC AGCCATCCAT    3600

TCTTCTATGT CAGCAGAGCC TGTAGAACCA AACATTATAT CCATCCTATC CAAAAGATCA    3660

TTAAATCTGT TTGTTAACAT TTGTTCTCTA GTTAATTGTA GGCTATCAAC CCGCTTTTTA    3720

GCTAAAACAG TATCAACAGC CTGTTGGCAT ATGGTTTTTT GGTTTTTGCT GTCAGCAAAT    3780

ATAGCAGCAT TTGCATAATG CTTTTCATGG TACTTATAGT GGCTGGGCTG TTCTTTTTTA    3840

ATACATTTTA AACACATTTC AAAACTGTAC TGAAATTCCA AGTACATCCC AAGCAATAAC    3900

AACACATCAT CACATTTTGT TTCCATTGCA TACTCTGTTA CAAGCTTCCA GGACACTTGT    3960

TTAGTTTCCT CTGCTTCTTC TGGATTAAAA TCATGCTCCT TTAACCCACC TGGCAAACTT    4020

TCCTCAATAA CAGAAAATGG ATCTCTAGTC AAGGCACTAT ACATCAAATA TTCCTTATTA    4080

ACCCCTTTAC AAATTAAAAA GCTAAAGGTA CACAATTTTT GAGCATAGTT ATTAATAGCA    4140

GACACTCTAT GCCTGTGTGG AGTAAGAAAA AACAGTATGT TATGATTATA ACTGTTATGC    4200

CTACTTATAA AGGTTACAGA ATATTTTTCC ATAATTTTCT TGTATAGCAG TGCAGCTTTT    4260

TCCTTTGTGG TGTAAATAGC AAAGCAAGCA AGAGTTCTAT TACTAAACAC AGCATGACTC    4320

AAAAAACTTA GCAATTCTGA AGGAAAGTCC TTGGGGTCTT CTACCTTTCT CTTCTTTTTT    4380

GGAGGAGTAG AATGTTGAGA GTCAGCAGTA GCCTCATCAT CACTAGATGG CATTTCTTCT    4440

GAGCAAAACA GGTTTTCCTC ATTAAAGGCA TTCCACCACT GCTCCCATTC ATCAGTTCCA    4500

TAGGTTGGAA TCTAAAATAC ACAAACAATT AGAATCAGTA GTTAACACA TTATACACTT    4560

AAAAATTTTA TATTTACCTT AGAGCTTTAA ATCTCTGTAG GTAGTTTGTC CAATTATGTC    4620

ACACCACAGA AGTAAGGTTC CTTCACAAAG ATCAAGTCCA AACCACATTC TAAAGCAATC    4680

GAAGCAGTAG CAATCAACCC ACACAAGTGG ATCTTTCCTG TATAATTTTC TATTTTCATG    4740

CTTCATCCTC AGTAAGCACA GCAAGCATAT GCAGTTAGCA GACATTTTCT TTGCACACTC    4800
```

-continued

```
AGGCCATTGT TTGCAGTACA TTGCATCAAC ACCAGGATTT AAGGAAGAAG CAAATACCTC      4860

AGTTGCATCC CAGAAGCCTC CAAAGTCAGG TTGATGAGCA TATTTTACTC CATCTTCCAT      4920

TTTCTTGTAC AGAGTATTCA TTTTCTTCAT TTTTTCTTCA TCTCCTCCTT TATCAGGATG      4980

AAACTCCTTG CATTTTTTTA AATATGCCTT TCTCATCAGA GGAATATTCC CCCAGGCACT      5040

CCTTTCAAGA CCTAGAAGGT CCATTAGCTG CAAAGATTCC TCTCTGTTTA AAACTTTATC      5100

CATCTTTGCA AAGCTTTTTG CAAAAGCCTA GGCCTCCAAA AAAGCCTCCT CACTACTTCT      5160

GGAATAGCTC AGAGGCCGAG GCG                                              5183
```

(2) INFORMATION FOR SEQ ID NO:19:

(i) SEQUENCE CHARACTERISTICS:
        (A) LENGTH: 2000 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
TTGCATGCCT GCAGGTATAC AATTTCCCAC AAAGTGTGAT TATACTGTAG TCGTCAAAGC        60

AGATAACAAC TCATCCCACA CTCCCTTAAT CCCCAGCCTG ATTTCAAACT CACCTGGCAT       120

AGCAAGGTTC TGTGCTAACT CCTACACTCA CTGTCTGTAT CCTAGAGGAC AAAGAATCTT       180

CACACATCTC CTTTCTGGGG AAGCAGGTTC TGCAGATGAA AAGGGTATTA GGATAAAAAC       240

CAGCTGGCTA CACTGTGCCT CTCAGCCACT ACCACCACCA AGATCCTGAC AACAGACACA       300

AGTTGCATTT TGACTTTTGT TTCTCAAAGC ATGATCTGCA AGCCGTCTGC ATGGGTAGCA       360

CCTGGGGGCC TTGATAATGA CCCCACTTTA GACCTATCGA ATTATCGTTT TTGGAGCCTA       420

CATCTTAAAG AGCTTCCAAG GTTATTTTGA ACATTTTTAT TATGGAAATT TTCAAATATA       480

CATTGAAGTA AGAAGTATGG GGTAATACCT TACCACGCAA AGTATGGTCG TAGGACAGCT       540

ACCTCACCAT CAGCTGGGGG CTTGTTAGAA GGGCAGAATC TTGGGCCGCA ACCGCAACCC       600

AGACATCCCG AATCAGAATC TGCATTTAGC AGGTCCTCAG GTGGTTAGTG TGCAAATTAA       660

ACCTTGAGAA GCACAGATAT ATGGACCCTC CTGCCCCCAT CACTCAACAG TCAGGGTCAA       720

TCTTGTATCA TCAATACCTT CCCCCAGCAC AGGATTATTT AAAAGCAAAT CCCTAACATT       780

AGGAATGTCT TTTTGTTTGT TTCACTCTAA TGCCCAGGCT GGAGTGCAGT GGCGCAACCT       840

CTGTCTCCCG AGTTCAAGCA GTTCTCATGC CTCAGCCTCC CAAGTAGCTG GGATTACAGG       900

TGTGTGCCAC CACAACCGGC TAAATTTTGT ATTTTTAGTA GAGACGGGGT TTCATCATGT       960

TGGCCAGGCT GGTTTTGAAC CCCTGACCTC ATGTAACCTG CCCGCCTCGG CCTCCCAAAG      1020

TGCTGGGATT ACAGGTGTGG GCCAACGCGT CCGGCCAATA ATTTATAAAT ATCACCTCGT      1080

CAATGTTCAA ATTTCCATTA ATAACCAATC TTTGAGGTCC TCTGGATTGC GATAAGGATT      1140

ATACCAAGAT GATTTAATTC CTCCACTTTC CCTGCAACGG AATTTCTTTT TACCCACGTG      1200

AGCTAGAGTC TCTGAGATGC TGCACACTAA AAGAAACACC AAACAAAGCT CTTGGAAGGG      1260

GCTAATGCCT CTCAGCATAA ACACACACAC CCGTCTCGCC CCAACACTTG CCACGCCGGC      1320

ACGAAACGCT CCATCTCCCG TGGAAGGCCA GCAAAACTTA GAAGAAAACG TCCGCGAAAA      1380

CGGCACGAGA AAGAAGCGAA GAAAATGAAA CGCTTACAAC ACCCTCCACC CAAAATAATC      1440

TCTCCTAGTA TTACCCTAGT GAATGGACAT CACTAGTAAG GCGCGGTTTA AATCTCCCGG      1500

GGTTCGTGGG GCTGAGGGAA CGAGGAAAAC AGAAAGGGTG TGGAGATTGG TGAGAGGGAG      1560
```

-continued

```
AGCCAATGAT GCGCCAGGCT CCCCGTGAGG CGGAGCTTAC CCCGCAGCCT GCCTAACGCT    1620

GGTGGGCCAA ACACTATCCT GCTCTGGCTA TGGGGCGGGG CAAGTCTTAC CATTTCCAGA    1680

GCAAGCACAC GCCCCCAGGT GATCTGCGAG CCCAACGATA GGCCATGAGG CCCTGGGCGC    1740

GCGCGCGGAG ATTGGCTGAC GCAGCTTAGA GGCGAGCGGG GATAGGTTAC TGGGCTGGCG    1800

GAAGGTTTGA ATGGTCAACG CCTGCGGCTG TTGATATTCT TGCTCAGAGG CCGTAACTTT    1860

GGCCTTCTGC TCAGGGAAGA CTCTGAGTCC GACGTTGGCC TACCCAGTCG GAAGGCAGAG    1920

CTGCAATCTA GTTAACTACC TCCTTTCCCC TAGATTTCCT TTCATTCTGC TCAAGTCTTC    1980

GCCTGTGTCC GATCCCTACT                                                 2000
```